United States Patent
Bahn

(10) Patent No.: US 10,435,027 B2
(45) Date of Patent: Oct. 8, 2019

(54) DRIVER ASSISTANCE APPARATUS

(71) Applicant: LG ELECTRONICS INC., Seoul (KR)

(72) Inventor: Jungsoo Bahn, Seoul (KR)

(73) Assignee: LG Electronics Inc., Seoul (KR)

( * ) Notice: Subject to any disclaimer, the term of this patent is extended or adjusted under 35 U.S.C. 154(b) by 140 days.

(21) Appl. No.: 15/074,852

(22) Filed: Mar. 18, 2016

(65) Prior Publication Data

US 2017/0096145 A1  Apr. 6, 2017

(30) Foreign Application Priority Data

Oct. 6, 2015  (KR) .................. 10-2015-0140106

(51) Int. Cl.
| | |
|---|---|
| B60W 40/08 | (2012.01) |
| G01N 33/497 | (2006.01) |
| E05F 15/70 | (2015.01) |
| B60Q 9/00 | (2006.01) |
| B60K 28/06 | (2006.01) |
| B60J 1/12 | (2006.01) |

(52) U.S. Cl.
CPC ............. *B60W 40/08* (2013.01); *B60J 1/12* (2013.01); *B60K 28/063* (2013.01); *B60Q 9/00* (2013.01); *E05F 15/70* (2015.01); *G01N 33/4972* (2013.01); *B60W 2040/0836* (2013.01)

(58) Field of Classification Search
CPC .......... B60W 40/08; B60W 2040/0836; E05F 15/70; B60K 28/063; G01N 33/4972; B60J 1/12; B60Q 9/00
See application file for complete search history.

(56) References Cited

U.S. PATENT DOCUMENTS

| | | | | |
|---|---|---|---|---|
| 2004/0083031 A1* | 4/2004 | Okezie | .................. | A61B 5/145 |
| | | | | 701/1 |
| 2004/0239510 A1* | 12/2004 | Karsten | ................ | B60K 28/063 |
| | | | | 340/576 |
| 2008/0250829 A1* | 10/2008 | Kamiki | ................ | B60K 28/063 |
| | | | | 70/344 |
| 2010/0010689 A1* | 1/2010 | Yasushi | ................ | B60K 28/063 |
| | | | | 701/1 |
| 2010/0012417 A1* | 1/2010 | Walter | ................. | B60K 28/063 |
| | | | | 180/272 |
| 2012/0242469 A1* | 9/2012 | Morgan | ................. | B60K 28/06 |
| | | | | 340/426.11 |
| 2013/0231871 A1* | 9/2013 | Hok | ....................... | A61B 5/087 |
| | | | | 702/19 |

(Continued)

FOREIGN PATENT DOCUMENTS

| | | |
|---|---|---|
| JP | 2009078630 | 4/2009 |
| JP | 2009097960 | 5/2009 |

(Continued)

*Primary Examiner* — Tuan C To
(74) *Attorney, Agent, or Firm* — Fish & Richardson P.C.

(57) ABSTRACT

A driver assistance apparatus, in which a sensor is configured to measure an alcohol concentration from a driver, and output the measured alcohol concentration. The apparatus includes a processor configured to perform a first drunk-driving test based on a first alcohol concentration received from the sensor before starting the vehicle, and perform a second drunk-driving test based on a second alcohol concentration received from the sensor while the vehicle is operating.

16 Claims, 17 Drawing Sheets

(56) References Cited

U.S. PATENT DOCUMENTS

| | | | | |
|---|---|---|---|---|
| 2015/0204844 A1* | 7/2015 | Nothacker | ......... | G01N 33/4972 |
| | | | | 73/23.3 |
| 2015/0226727 A1* | 8/2015 | Son | .................. | G01N 33/0008 |
| | | | | 73/23.3 |
| 2015/0233897 A1* | 8/2015 | Hok | .................. | G01N 21/3504 |
| | | | | 73/23.3 |
| 2017/0096145 A1* | 4/2017 | Bahn | ....................... | E05F 15/70 |
| 2017/0326978 A1* | 11/2017 | Nienhouse | ............... | H04Q 9/00 |

FOREIGN PATENT DOCUMENTS

| | | |
|---|---|---|
| JP | 2009-255864 | 11/2009 |
| KR | 20-0330745 | 10/2003 |
| KR | 10-2012-0057602 | 6/2012 |
| KR | 10-2014-0021720 | 2/2014 |
| KR | 10-1448793 | 10/2014 |
| KR | 10-1525204 | 6/2015 |
| KR | 10-2015-0083929 | 7/2015 |
| KR | 10-2015-0086911 | 7/2015 |
| KR | 10-1535296 | 7/2015 |

\* cited by examiner (a)

(b)

(a)

(b)

(C)

DRIVER ASSISTANCE APPARATUS

CROSS-REFERENCE TO RELATED APPLICATIONS

The present application claims priority under 35 U.S.C. 119 and 35 U.S.C. 365 to Korean Patent Application No. 10-2015-0140106 (filed on Oct. 6, 2015), which is hereby incorporated by reference in its entirety.

TECHNICAL FIELD

The present disclosure relates to a driver assistance apparatus. The driver assistance apparatus can be used in relation to a vehicle.

BACKGROUND

A vehicle is an apparatus that is moved in a direction in which a driver wants to go. An example of the vehicle is a car.

In addition, for the convenience of a user who uses a vehicle, the inclusion of various sensors and electronic devices is a modern trend. In particular, various devices for the driving convenience of a user are being developed.

SUMMARY

In one aspect, a driver assistance apparatus includes a sensor configured to measure an alcohol concentration from a driver, and output the measured alcohol concentration. The driver assistance apparatus also includes a processor configured to perform a first drunk-driving test based on a first alcohol concentration received from the sensor before starting the vehicle, and perform a second drunk-driving test based on a second alcohol concentration received from the sensor while the vehicle is operating.

Implementations may include one or more of the following features. For example, the processor may be configured to prevent, based on a determination that the first alcohol concentration does not satisfy a critical value, the starting of the vehicle, and enable, based on a determination that the first alcohol concentration satisfies the critical value, the starting of the vehicle. In this example, the processor may be configured to, based on a result of the first alcohol concentration, set a test condition for the second drunk-driving test, the test condition comprising at least one of a second drunk-driving test cycle, a number of second drunk-driving tests, a sensitivity level of the sensor, or the critical value.

In some implementations, the sensor may include at least one of a first sensor disposed at a door handle of the vehicle, a second sensor disposed at a steering wheel of the vehicle, a third sensor disposed inside the vehicle to receive a touch signal, or a fourth sensor disposed inside the vehicle to measure an alcohol level in air inside the vehicle. In these implementations, the processor may be configured to, based on the first alcohol concentration, perform the first drunk-driving test before the start of the vehicle, the first alcohol concentration being received from one of the first sensor, the second sensor, the third sensor, or the fourth sensor.

Also, the processor may be further configured to perform, based on a determination that the first alcohol concentration is measured before the driver gets in the vehicle, a third drunk-driving test after the driver gets into the vehicle. In addition, the processor may be further configured to verify, based on the determination that the first alcohol concentration satisfies the critical value, that the first alcohol concentration is an alcohol concentration of the driver in a driver's seat.

In some examples, the driver assistance apparatus may include a user authentication unit that is configured to identify the driver in a driver's seat of the vehicle. In these examples, the user authentication unit may include at least one of a first user authentication unit configured to capture an image of the driver in the driver's seat and identify the driver based on the captured image, or a second user authentication unit configured to recognize a fingerprint of the driver in the driver's seat.

In some implementations, the processor may be configured to restrict, based on a determination that the driver in the driver's seat of the vehicle is an unregistered driver, starting of the vehicle. In these implementations, the user authentication unit is further configured to identify, based on a determination that the driver in the driver's seat is a registered user, a passenger in a passenger seat of the vehicle, and the processor may be configured to enable, based on a determination that the passenger in the passenger seat is the registered user, starting of the vehicle.

In some examples, the sensor may be configured to sense at least one of information about the driver touching a touch sensor, information about a driving pattern based on a usage of a steering wheel, information about an alcohol level in air inside the vehicle, or information about a conversation pattern of a passenger in the vehicle, and output, to the processor, the information for the second drunk-driving test. In these examples, the processor may be configured to perform the second drunk-driving test at a preset test time, wherein the preset test time is at least one of a first time corresponding to an irregular time, a second time corresponding to a preset cycle, a third time corresponding to a time that the vehicle stops, and a fourth time corresponding to a time that a door of the vehicle opens.

In some implementations, the processor may be configured to monitor whether one or more windows of the vehicle are opened or closed during performance of the second drunk-driving test, and control, in response to monitoring whether the one or more windows of the vehicle are opened or closed during performance of the second drunk-driving test, the one or more windows. In these implementations, the processor may be configured to exclude, in response to monitoring whether the one or more windows of the vehicle are opened or closed during performance of the second drunk-driving test, the information about the alcohol level in air in the vehicle for the second drunk-driving test.

Also, the driver assistance apparatus may include a guide information output unit configured to provide the driver with guide information, the guide information providing instruction on how the driver provides a user input to the sensor. Further, the driver assistance apparatus may include a warning signal output unit that is configured to output, based on a determination that a user input for the second drunk-driving test is received or a determination that the second alcohol concentration satisfies a critical value, a warning signal. The warning signal output unit may include a communication unit transmitting a result of the second drunk-driving test to a designated organization, a related organization, or a stored contact.

In addition, the processor may be configured to switch, based on a determination of a failure of the second drunk-driving test, a driving mode of the vehicle to a self-driving mode. The processor may be configured to stop, based on a determination of a failure of the second drunk-driving test, the vehicle in a safe region.

In another aspect, a drunk-driving prevention method includes performing a first drunk-driving test before starting of a vehicle, enabling, based on a determination that the first drunk-driving test has been passed, the starting of the vehicle, and performing a second drunk-driving test while the vehicle is operating after the starting of the vehicle.

Implementations may include one or more of the following features. For instance, the drunk-driving prevention method may include setting, based on the first alcohol concentration, a test condition for the second drunk-driving test based on the result of the first drunk-driving test, wherein the test condition comprises at least one of a second drunk-driving test cycle, a number of times the second drunk-driving test is performed, a sensitivity level of a sensor, or a critical value.

The drunk-driving prevention method may include performing, based on a determination that the first alcohol concentration is measured before the driver gets into the vehicle, a third drunk-driving test after the driver gets into the vehicle. Also, the drunk-driving prevention method may include identifying the driver in a driver's seat of the vehicle, identifying, based on a determination that the identified driver in the driver's seat of the vehicle is a registered user, a passenger in a passenger seat of the vehicle, and enabling, based on a determination that the passenger in the passenger seat of the vehicle is the registered user, the starting of the vehicle. Further, the second drunk-driving test may be performed at a test time, wherein the test time is at least one of a time that the vehicle stops, or a time that a door of the vehicle opens.

In some examples, the drunk-driving prevention method may include outputting, based on a determination that a user input for the second drunk-driving test is received or a determination that the second alcohol concentration satisfies a critical value, a warning signal. In these examples, the drunk-driving prevention method may include transmitting a result of the second drunk-driving test to a designated organization, a related organization, or a stored contact. The drunk-driving prevention method may include switching, based on a determination of a failure of the second drunk-driving test, a driving mode of the vehicle to a self-driving mode, or stopping, based on a determination of a failure of the second drunk-driving test, the vehicle in a safe region.

DETAILED DESCRIPTION

A vehicle may include a car or motorcycle. The vehicle may include all of an internal combustion engine vehicle that includes an engine as a power source, a hybrid vehicle that includes an engine and an electrical motor as a power source, and an electrical vehicle that includes an electrical motor as a power source.

In the following description, the right side of the vehicle may indicate the left side of the driving direction of the vehicle and the right side of the vehicle may indicate the right side of the driving direction of the vehicle.

In the following description, a left hand drive (LHD) vehicle is mostly described unless mentioned to the contrary.

Figure 1:
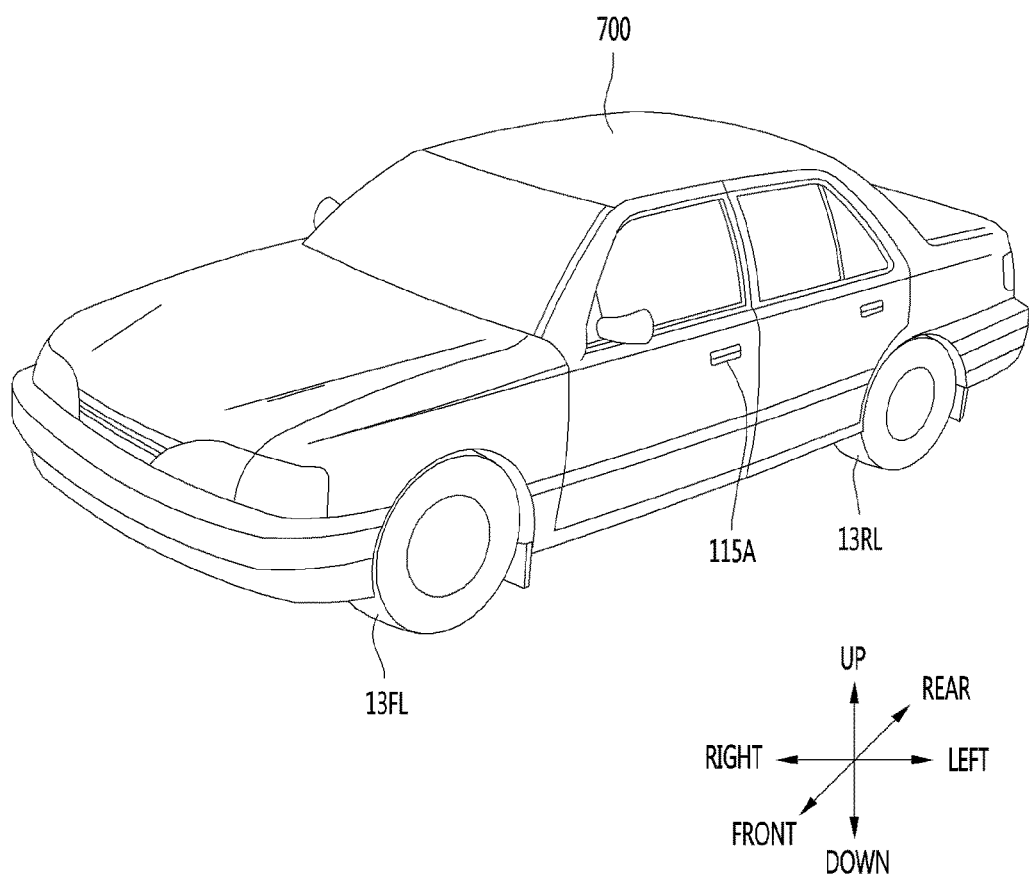
FIG. 1 is a diagram illustrating an example exterior of a vehicle that includes a driver assistance apparatus.
Figure 2:
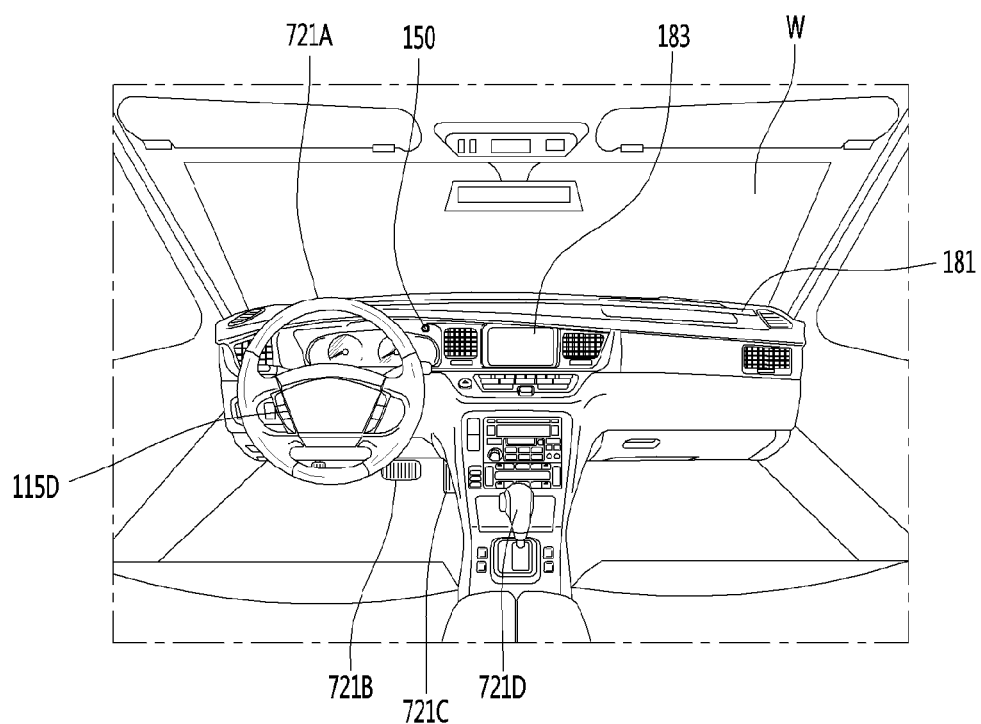
FIG. 2 is a diagram illustrating an example interior of a vehicle that includes a driver assistance apparatus.
Figure 3:
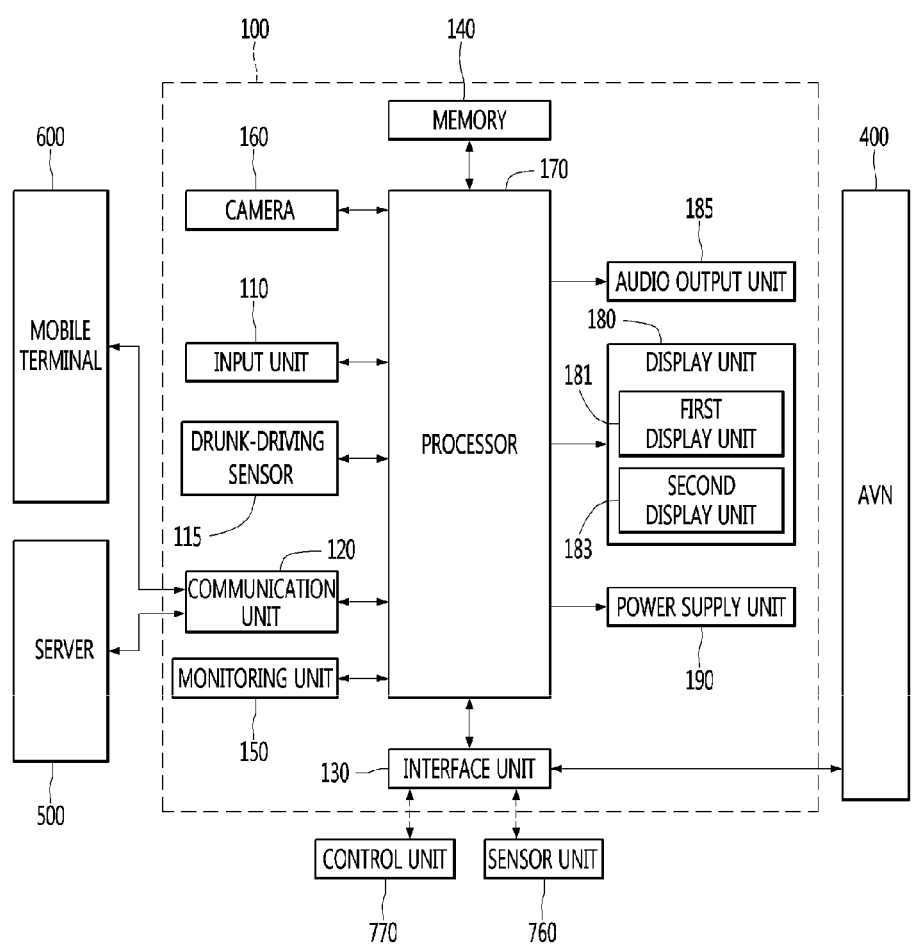
FIG. 3 is a diagram illustrating an example driver assistance apparatus.

FIG. 1 is a diagram illustrating the exterior of a vehicle that includes a driver assistance apparatus, FIG. 2 is a diagram illustrating the interior of a vehicle that includes a driver assistance apparatus, and FIG. 3 illustrates a block diagram of a driver assistance apparatus.

Referring to FIGS. 1 to 3, a vehicle 700 may include wheels 13FL and 13FR that rotate by a power source, driving manipulation units 721A to 721D for controlling the driving of the vehicle 700, and a driver assistance apparatus 100.

The vehicle 700 as described in the present disclosure is a vehicle 700 that may provide advanced driver assistance systems (ADAS). For example, the vehicle 700 may provide a blind spot detection (BSD) function, a lane keeping assist system (LKAS), a lane departure warning system (LDWS), an auto emergency braking (AEB) function, etc.

These ADAS may be executed by the driver assistance apparatus 100, in the vehicle 700 or by a separate device.

In the following, although the driver assistance apparatus 100 is described to perform the drunk-driving test of a driver or passenger in a vehicle and control the driving right of the vehicle based on a result of the drunk-driving test.

Also, although the driver assistance apparatus 100 is described to include units as shown in FIG. 3, it is also possible to use the units of the vehicle 700 through the interface unit 130. Also, the driver assistance apparatus 100 may also be understood to be a set of the units of the vehicle 700.

Referring to FIG. 3, such a driver assistance apparatus 100 may include an input unit 110, a drinking sensor 115, a communication unit 120, an interface unit 130, a memory 140, a monitoring unit 150, a camera 160, a processor 170, a display unit 180, an audio output unit 185, and a power supply unit 190.

Firstly, the driver assistance apparatus 100 may include the input unit 110 that senses a user's input. A user may enable/disable a driver assistance function through the input unit or perform an input for executing the power on and off of the driver assistance apparatus 100.

An input unit 110 may include at least one of a gesture input unit 111 that senses a user gesture, a touch input unit 110 that senses a touch, and a microphone 115 that senses a voice input, and thus sense a user input.

In some implementations, the touch input unit 110 in the input unit 110 touches a specific portion of a display screen to generate a control command allocated to the specific portion. Also, the touch input unit 110 may also operate as the drinking sensor 120 that determines drinking based on a touch signal from a user and also operate as a user authentication unit that receives a fingerprint based on a user touch to perform user authentication.

In other words, the processor 170 may output a control signal for controlling the specific component of the vehicle 700 based on a user input that is input through the input unit 110.

In some implementations, the processor 170 may check the drinking state of a passenger in the vehicle 700 based on a user unit input through the input unit 110 to output a control signal for controlling the vehicle 700. Thus, the input unit 110 is configured to perform a function corresponding to the drinking sensor 120 as well as simply performing a function for the user input to receive information for checking the drinking state of the passenger.

The drinking sensor 120 checks the drinking state of the passenger in the vehicle 700 and outputs the checked information on the drinking state to the processor 170. In this example, the passenger includes a driver in a driver's seat and passengers in a seat next to the driver's seat or in rear seats.

In some implementations, the information output from the drinking sensor 120 may be the alcohol concentration of the passenger or various pieces of information that may be used for checking the drinking state.

The drinking sensor 120 may be disposed inside the vehicle 700, outside the vehicle 700, or in a separate external device.

In other words, the drinking sensor 120 may check the drinking state of a passenger in the vehicle 700 or check the drinking state of a person outside the vehicle 700 who waits for getting in the vehicle 700.

Figure 4:
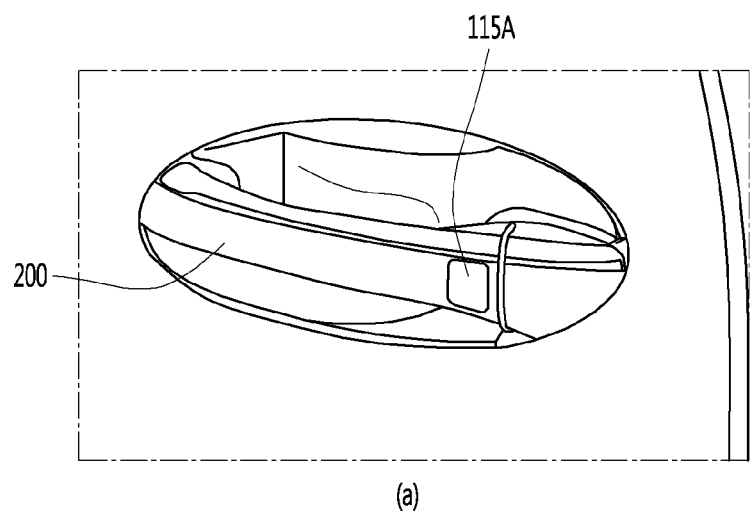
FIG. 4 is a diagram illustrating an example drinking sensor.
Figure 4:
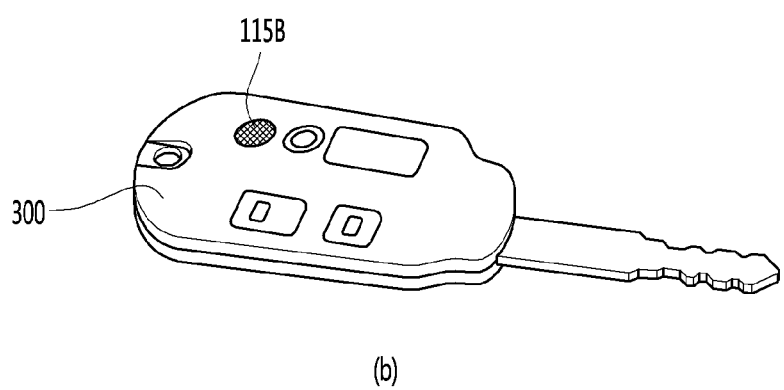

FIG. 4 shows an example of the drinking sensor 120.

Referring to FIG. 4, the drinking sensor 120 for checking the drinking state as described above may include a first drinking sensor 115A that is disposed at the door handle 200 of the vehicle 700, and a second drinking sensor 115B that is disposed at a remote key 300.

Also, the drinking sensor 120 may include a touch input unit that configures the input unit 110, and a microphone that configures the input unit 110.

Also, the drinking sensor 120 may include an alcohol concentration sensor that senses the concentration of alcohol in the air inside the vehicle, and a steering wheel sensor that senses the state of a steering wheel.

The drinking sensor 120 obtains information for checking the drinking state of a passenger inside the vehicle 700 or a person who waits for getting in the vehicle 700, and provides the obtained information to the processor 170.

The touch input unit may be disposed at a start button for the start on of the vehicle 700 or may be disposed at a portion of the steering wheel (a fourth drinking sensor 115D as shown in FIG. 2).

In addition, the drinking sensors 120 may be divided into a sensor that is disposed inside the vehicle, and a sensor (including a remote key) that is disposed outside the vehicle.

In some implementations, the drinking sensors 120 may be divided into a sensor that operates for the first drunk-driving test of the passenger before the start on of the vehicle 700, and a sensor that operates for the second drunk-driving test of the passenger during the driving of the vehicle 700.

In this example, the sensors that operate for the first drunk-driving test may include a sensor outside the vehicle and some of sensors inside the vehicle, and the sensors that operate for the second drunk-driving test may include some of the sensors inside the vehicle, excluding the sensors outside the vehicle.

The particular operations of the drinking sensor 120 and the corresponding operations of the processor 170 are described below in more detail.

Next, the driver assistance apparatus 100 may include a communication unit 120 that performs communication with another vehicle 510, a terminal 600, a server 500, etc. The driver assistance apparatus 100 may receive navigation information and/or traffic information through the communication unit 120.

Also, the communication unit 120 may store, in the server 500, information on a result of the drunk-driving test performed based on the information obtained through the drinking sensor 120 through the communication with the server 500, and receive specific destination information from the server 500 to transmit the information on the result of the drunk-driving test to the specific destination.

In some implementations, the specific destination may be drunk-driving related organizations (e.g., a police station or insurance company), other vehicles driving near the vehicle 700, or a mobile terminal of a specific user whom a user has previously registered.

Specifically, the communication unit 120 may wirelessly exchange data with the mobile terminal 600, the server 500 or the specific related organizations. In particular, the communication unit 120 may wirelessly exchange data with the mobile terminal 600 of the vehicle 700 driver. The wireless data communication scheme may include various data communication schemes, such as Bluetooth, WiFi, Direct WiFi, APiX, or NFC schemes.

Also, the communication unit 120 may receive position information, weather information, or road traffic information, e.g., transport protocol expert group (TPEG) information, from the mobile terminal 600 or the server 500.

Also, the communication unit 120 may also receive navigation information from the mobile terminal 600, when the mobile terminal 600 is used as a navigation device. In this example, the navigation information may include at least one of map information relating to vehicle 700 driving, position information on the vehicle 700, set destination information, and route information depending on a destination.

Also, when a user gets in the vehicle 700, the mobile terminal 600 of the user and the driver assistance apparatus 100 may also perform pairing automatically or by the execution of an application by the user.

The communication unit may transmit a driver assistance function operation history to the mobile terminal 600 through pairing to provide the history to the user.

Next, the driver assistance apparatus 100 may include the interface unit 130 that receives vehicle related data or transmits a signal processed or generated by the processor 170 to the outside.

The interface unit 130 is configured to perform data communication with the control unit 770, an audio video navigation (AVN) device 400 and/or the sensor unit 760 in the vehicle 700 through wired or wireless communication.

The interface unit 130 may receive navigation information through data communication with the control unit 770, the AVN device 400 and/or a separate navigation device.

Also, the interface unit 130 may receive sensor information from the control unit 770 or the sensor unit 760.

In this example, the sensor information may include at least one of vehicle 700 direction information, position information, speed information, acceleration information, tilt information, forward/backward movement information, fuel information, information on the distance to front and rear vehicles 700, information on the distance between a vehicle 700 and a lane, and turn signal information.

In addition, the sensor information from the sensor unit 760 may be utilized as information that may check the drinking of the passenger.

For example, the distance to the front vehicle 700 based on an AEB operation history among the driver assistance functions may be utilized as information for analyzing the driving pattern of the vehicle 700, and the processor 170 may compare the driving pattern with a pre-stored driving pattern history to check the drinking.

Also, the sensor information may be acquired from a heading sensor, a yaw sensor, a gyro sensor, a position module, a vehicle's forward/backward movement sensor, a wheel sensor, a vehicle 700 speed sensor, a vehicle-body tilt sensor, a battery sensor, a fuel sensor, a tire sensor, a steering sensor by the rotation of a steering wheel, a vehicle 700 internal temperature sensor, a vehicle 700 internal humidity sensor, etc. The position module may include a GPS module for GPS information reception.

The interface unit 130 may receive a user input received through the user input unit 110 of the vehicle 700. The interface unit 130 may receive the user input from a user input unit 720 (see FIG. 19) of the vehicle 700 or through a control unit 770 (see FIG. 19). That is, in case that the input unit 110 is disposed as a component of the vehicle 700 therein, it is possible to receive the user input through the interface unit 130.

The interface unit 130 may also receive traffic information acquired from the server 500. The server 500 may be a server that is located at a traffic control center controlling traffic. For example, in case that the traffic information is received from the server 500 through the communication unit 120 of the vehicle 700, the interface unit 130 may also receive the traffic information from the control unit 770.

Next, the memory 140 may store various pieces of data for the overall operations of the driver assistance apparatus 100, such as programs for processing or controlling by the processor 170. Also, the memory 140 may further store information on a pre-registered user, information on the driving pattern of a driver, etc.

In this example, a driving pattern history may include at least one of a history of direction of a driver who usually drives the vehicle 700, a history of position, a history of speed, a history of acceleration, a history of tilt, a history of forward/backward movement, a history of fuel, a history of the distance to front and rear vehicles 700, a history of the distance between a vehicle 700 and a lane, and a history of turn signal.

The memory 140 may be various storage devices, such as ROMs, RAMS, EPROMs, flash drives, hard drives, etc. that are hardware.

Next, the driver assistance apparatus 100 may include the monitoring unit 150 that captures an internal image of the vehicle 700.

Specifically, the monitoring unit 150 may sense and acquire driver's biometric information. In addition, the acquired biometric information may be utilized as authentication information for performing user authentication.

The biometric information may include image information including an image of a user, fingerprint information, iris-scan information, retina-scan information, hand geometry information, facial recognition information, and voice recognition information. That is, the monitoring unit 150 may include a sensor that senses driver's biometric information.

Also, the monitoring unit 150 may acquire the image of the user for biometrics. That is, the monitoring unit 150 may be an image acquisition module that is disposed inside the vehicle 700.

Also, it is possible to analyze an image of a user acquired through the monitoring unit 150 to detect a line of sight of the user. In addition, the processor 170 is configured to control the display unit 180 so that projected images are displayed on the wind shield W based on the detected line of sight.

Next, the driver assistance apparatus 100 may include a camera 160 that captures images around the vehicle 700. The images around the vehicle 700 captured through the camera 160 may be include in driver assistance function related images.

Such a camera 160 may further include a plurality of cameras 160.

For example, the plurality of cameras 160 may be disposed at at least one of the left, rear, right and front of the vehicle 700. That is, it is possible to capture images of the front, rear, left and right of the vehicle 700 and store, an image captured in an optimal visual field direction for checking a driver assistance function operation, as an driver assistance function related image. For example, it is possible to store an image of a side of the vehicle 700 as a driver assistance function related image when the LKAS operates.

In some implementations, the left camera may be disposed in a casing that surrounds a left side mirror. In some implementations, the left camera may be disposed outside a casing that surrounds a left side mirror. In some implementations, the left camera may be disposed on a region outside a left front door, left rear door or left fender.

The right camera may be disposed in a casing that surrounds a right side mirror. In some implementations, the right camera may be disposed outside a casing that surrounds a right side mirror. In some implementations, the right camera may be disposed on a region outside a right front door, right rear door or right fender.

Also, the rear camera may be disposed near a rear number plate or trunk switch. The front camera may be disposed near an emblem or radiator grill.

As such, an image captured in at least one of all directions may be processed by the processor 170 and provided as a view point image so that a user may intuitively recognize a driver assistance function. For example, the processor 170 may synthesize images captured in all directions to provide an around view image from a top view of the vehicle 700. When the around view image is generated, boundaries are generated among image regions. These boundaries may be naturally displayed by image blending.

For example, when the AEB function operates, it is possible to show a change before and after the operation of the vehicle 700 on a plane image representing a vehicle 700 and a front vehicle 700 so that a user may easily recognize the start time, effect, etc. of the AEB function.

Such a camera 160 may include an image sensor and an image processing module. The camera 160 may process a still image or video that is obtained by an image sensor (e.g., CMOS or CCD). The image processing module may process the still image or video obtained by the image sensor to extract necessary information, and deliver the extracted information to the processor 170.

Next, the driver assistance apparatus 100 may further include a display unit 180 that displays, as images, guide information for drunk-driving test or information on a result of the drunk-driving test.

Specifically, the display unit 180 may display an image that describes a drunk-driving test method in order to perform drunk-driving test, and an image that notifies the result of the drunk-driving test.

Such a display unit 180 may include a plurality of displays.

Specifically, the display unit 180 may include a first display unit 181 that projects and displays an image onto the windshield W of the vehicle 700. That is, the first display unit 181 may include a projection module projecting an image onto the windshield W, as a head up display (HUD).

In addition, since a projected image projected by the projection module has certain transparency, a user may simultaneously see the projected image and a view after the projected image.

The projected image displayed on such a first display unit 181 may overlap a reflected image reflected to the windshield W to implement augmented reality (AR). In some implementations, the projected image, such as information on the result of the drunk-driving test that is shown to a user may match a transparent image to intuitively deliver a description of a driver assistance function to the user.

Also, the first display unit 181 may display driver assistance information that includes a distance to a lane, a distance to an adjacent vehicle 700, etc.

Since the display unit 180 may enable the driver assistance function to be intuitively understood with a simple display and maintain the safe driving of the user, it is possible to enhance the safety of driving.

The display unit 180 may include a second display unit 183 that is separately installed inside the vehicle 700 and displays an image.

Specifically, the second display unit 183 may be the display of a vehicle 700 navigation apparatus or the front cluster inside the vehicle 700.

Also, the second display unit 183 may include at least one of a liquid crystal display (LCD), a thin film transistor-liquid crystal display (TFT LCD), an organic light-emitting diode (OLED), a flexible display, a 3D display, and an e-ink display.

Such a second display unit 183 may be coupled to the gesture input unit 110 to form a touch screen.

The user may search for a history of drunk-driving test through the touch screen and check related information. Also, the user may check various pieces of information (a method manual or information on a result of authentication) related to drunk-driving test through the touch screen.

Also, the driver assistance apparatus 100 may further include the audio output unit 185 and the power supply unit 190.

Specifically, the audio output unit 185 may output, through audio, a description on a drunk-driving test method, or a message checking the execution of the authentication and a result of authentication. The driver assistance apparatus 100 may supplement a description on drunk-driving test related information through the audio direction of the audio output unit 185, in addition to a visual display through the display unit 180.

Lastly, the driver assistance apparatus 100 may include the processor 170 that controls the overall operations of each unit in the driver assistance apparatus 100.

The processor 170 may be implemented by using at least one of an application specific integrated circuit (ASIC), a digital signal processor (DSP), a digital signal processing device (DSPD), a programmable logic device (PLD), a field programmable gate array (FPGA), the processor 170, a controller, a micro-controller, a microprocessor 170, and electrical units for executing other functions.

In addition, such a processor 170 may be controlled by a control unit or control various functions of the vehicle 700 through the control unit.

In particular, the processor 170 controls the operation of the drunk-driving sensor 120 and thus enables information for drunk-driving test to be acquired through the drunk-driving sensor 120.

Also, the processor 170 may use information acquired through the drunk-driving sensor 120 to control the operation of the vehicle 700. In this example, the operation control of the vehicle 700 may include a door open restriction, a start restriction, a driving restriction, etc.

That is, the processor 170 may restrict the door open of the vehicle 700 to disable a driver to get in the vehicle 700 based on a result of the drunk-driving test.

Also, the processor 170 may restrict the start on of the vehicle 700 to disable a driver in the vehicle 700 to start the start of the vehicle 700 based on a result of the drunk-driving test.

Also, the processor 170 may restrict the continuous driving of the vehicle 700 that is currently driving, based on a result of the drunk-driving test. In this example, restricting the driving may include switching the driving mode of the vehicle 700 to a self-driving mode and leading to the stop or parking of the vehicle 700 in a stable region so that the vehicle 700 may no longer drive.

The processor 170 performs the drunk-driving test many times for the drunk-driving test.

That is, the processor 170 performs first drunk-driving test before a driver gets in the vehicle 700 or before a driver in the vehicle 700 turns on the start of the vehicle 700.

In addition, the processor 170 outputs a control signal for controlling the operation of the vehicle 700 based on a result of the first drunk-driving test.

For example, the processor 170 allows the door open or start on of the vehicle to be normally performed when the result of the first drunk-driving test satisfies the normal criteria (e.g., a driver has not drunk).

In some implementations, when the result of the first drunk-driving test does not satisfy the normal criteria (e.g., the driver is drunk), the processor 170 disables the door open or start on of the vehicle. That is, the processor 170 restricts the door open or start on of the vehicle when the driver has drunk.

When the result of the first drunk-driving test satisfies normal criteria, the processor 170 allows the start on of the vehicle 700, and performs a second drunk-driving test after the start on of the vehicle 700.

That is, when the driver has drunk in the vehicle or the first drunk-driving test has been performed on the driver immediately after drinking, an accurate drinking state check is not performed through the first drunk-driving test and thus the processor 170 further performs a second drunk-driving test after the start on of the vehicle (or during the driving).

In some implementations, the processor 170 sets a test condition for performing the second drunk-driving test based on a result of the first drunk-driving test.

In this example, the test condition may include the second drunk-driving test cycle, the number of second drunk-driving tests, the sensitivity level of the drinking sensor 120, the size of a critical value, etc.

That is, the first drunk-driving test may be performed by the comparing of an alcohol concentration acquired based on the information sensed through the drinking sensor 120 with a preset, critical value. For example, when the acquired alcohol concentration exceeds the critical value, the processor 170 may determine that a driver has drunk, and when the acquired alcohol concentration is lower than or equal to the critical value, it is possible to determine that the driver has not drunk.

In addition, the processor 170 may set the test condition based on the acquired alcohol concentration when the first drunk-driving test satisfies the normal criteria.

For example, when the alcohol concentration is low (when a difference to the critical value is large), it is possible to increase the second drunk-driving test cycle, decrease the number of second drunk-driving tests, decrease the sensitivity level or increase the size of the critical value.

Also, when the alcohol concentration is high (when a difference to the critical value is small), it is possible to decrease the second drunk-driving test cycle, increase the number of second drunk-driving tests, increase the sensitivity level or decrease the size of the critical value.

In addition, the processor 170 performs the second drunk-driving test on the driver during the driving of the vehicle 700 based on the set test condition.

The second drunk-driving test may be performed by the drinking sensor 120 in the vehicle 700.

In some implementations, the second drunk-driving test may be performed through the analysis of an alcohol concentration in the air inside the vehicle, an alcohol concentration acquired through the biometric signal of the driver, the driving pattern of the vehicle 700, the voice of a passenger in the vehicle, etc.

The second drunk-driving test is described below in more detail.

In addition, the processor 170 controls the operation of the vehicle 700 that is driving, based on a result of the second drunk-driving test.

That is, when the result of the second drunk-driving test satisfies the normal criteria, the processor 170 maintains the current driving condition of the vehicle 700 as it is. On the contrary, when the result of the second drunk-driving test does not satisfy the normal criteria, the processor 170 changes the current driving condition of the vehicle 700.

The processor 170 performs user authentication on the driver on which the drunk-driving test has been performed and on passengers in the vehicle, when the first drunk-driving test and the second drunk-driving test are performed.

In addition, the processor 170 determines that the results of the first and the second drunk-driving tests satisfy the normal criteria, only when there are pre-registered users in the vehicle as a result of the user authentication.

Also, the processor 170 performs the first drunk-driving test many times based on the type of the drinking sensor 120 used in the first drunk-driving test when the first drunk-driving test is performed.

That is, when the first drunk-driving test is performed outside the vehicle, a driver in the driver's seat of the vehicle may be different from a person on which the first drunk-driving test has been performed outside the vehicle and thus the first drunk-driving test is re-performed after the driver gets in the vehicle.

Also, the processor 170 outputs information that enables the second drunk-driving test to be normally performed, when the second drunk-driving test is performed.

Also, the processor 170 outputs, to the outside, information notifying that the result of the second drunk-driving test does not satisfy the normal criteria, when the result of the second drunk-driving test does not satisfy the normal criteria.

In this example, the output of the information includes wirelessly transmitting the information to a preset mobile terminal or a related organization through the communication unit 120 or displaying the information in the form of an image through a separate display inside the vehicle.

Also, the it is possible to increase accuracy in drunk-driving test by performing the first drunk-driving test before the start of the vehicle and further performing the second drunk-driving test during the driving of the vehicle.

Also, it is possible to provide an optimal drunk-driving test environment depending on the situation, by applying a result of the first drunk-driving test to change the condition for the second drunk-driving test.

Also, it is possible to prevent counterfeit actions, such as a test by another person by further performing the first drunk-driving test after the driver gets in the vehicle, when the first drunk-driving test is performed before the driver gets in the vehicle.

Also, it is possible to prevent vehicle theft by performing user authentication on a driver and passengers to allow the start of the vehicle only when there are registered users inside the vehicle.

Also, it is possible to efficiently prepare for the replacement of a driver that may occur during the driving of the vehicle, by further performing the second drunk-driving test when the door of the vehicle opens or the vehicle stops.

Also, it is possible to prevent an accident that may occur by the drunk-driving of the driver, by restricting the driving of the vehicle, transmitting information on the vehicle to a related organization or changing the driving mode of the vehicle to a self-driving mode, when the result of the second drunk-driving test on the driver does not satisfy the normal criteria.

In the following, the first and second drunk-driving tests are described in more detail with reference to the accompanying drawings.

FIGS. 5 to 18 are diagrams for explaining a drunk-driving prevention method of a driver assistance apparatus.

Figure 5:
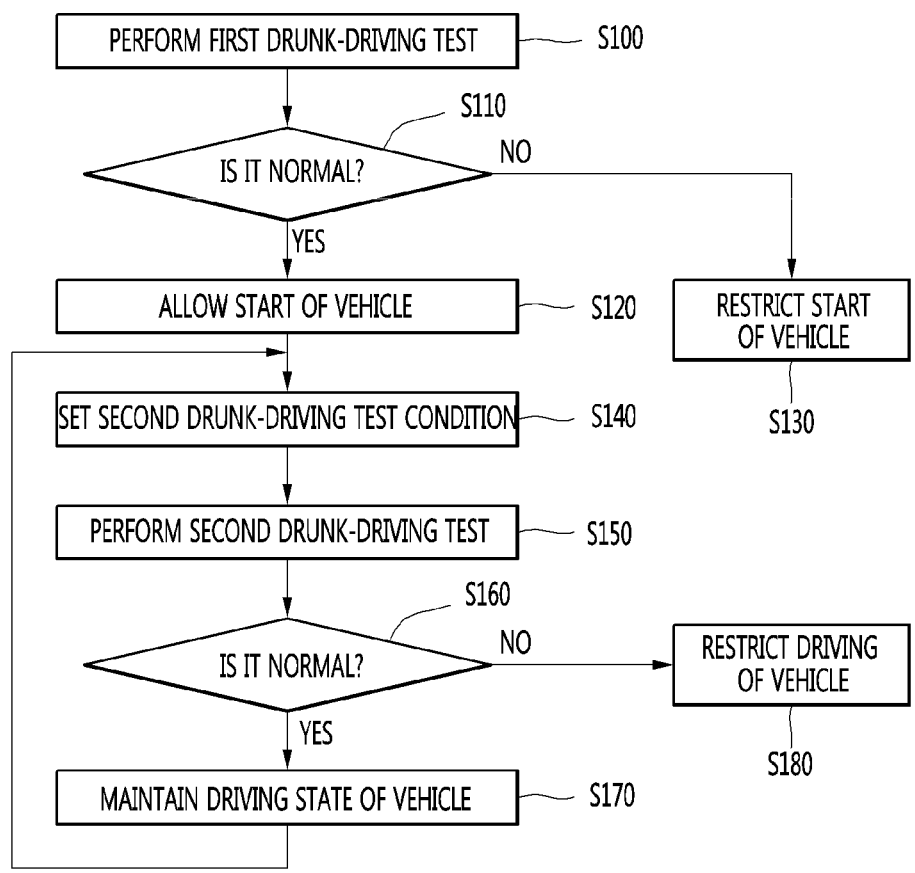
FIGS. 5 to 18 are diagrams and flowcharts illustrating an example operational process of a driver assistance apparatus.
Figure 6:
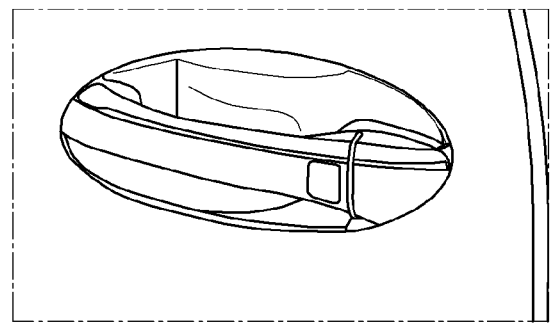
Figure 6:
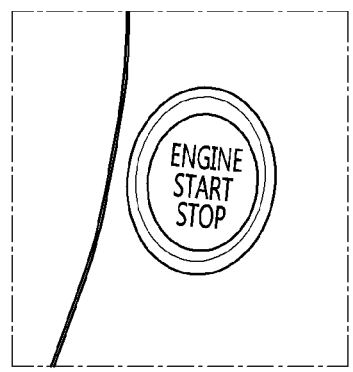
Figure 6:
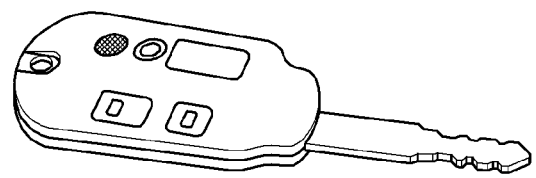

Referring to FIG. 5, the processor 170 performs a first drunk-driving test on the driver of the vehicle 700 before the start of the vehicle 700 in step S100.

To this end, the processor 170 actuates the drinking sensor 120 to acquire information for performing the first drunk-driving test. In some implementations, the first drunk-driving test may be performed inside the vehicle or in some implementations, it may be performed outside the vehicle.

FIGS. 6a to 6c are diagrams for explaining a first drunk-driving test method.

Referring to FIGS. 6a to 6c, the drinking sensor 120 may include a handle sensor disposed at the external door handle of the vehicle as shown in FIG. 6a, a touch sensor disposed at an start button inside the vehicle as shown in FIG. 6b, and a remote key sensor disposed at a separate vehicle remote key for controlling the vehicle as shown in FIG. 6c.

Thus, the first drunk-driving test may be performed outside the vehicle by the handle sensor and the remote key sensor before a driver gets in the vehicle and alternately, it may also performed inside the vehicle by the touch sensor after the driver gets in the vehicle.

The processor 170 receives information acquired through the drinking sensor 120 and performs a drunk-driving test on the driver of the vehicle by using the received information. That is, the processor 170 compares the alcohol concentration acquired through the drinking sensor 120 with a preset, critical value to determine the drinking of the driver.

In addition, the processor 170 determines whether the result of the first drunk-driving test performed by using the received information satisfies the normal criteria, in step S110. In other words, the processor 170 determines whether the driver of the vehicle has not drunk.

In addition, when as a result of the determination in step S110, the result of the first drunk-driving test satisfies normal criteria, the processor 170 allows the start of the vehicle 700, in step S120.

In some implementations, when as a result of the determination in step S110, the result of the first drunk-driving test does not satisfy the normal criteria, the processor 170 restricts the start of the vehicle 700, in step S130. In other words, the processor 170 disables the start on of the vehicle when it is checked that the driver has drunk.

When the result of the first drunk-driving test satisfies normal criteria, the processor 170 sets a test condition for a second drunk-driving test to be further performed during the driving of the vehicle 700, in step S140.

In this example, the test condition may include the second drunk-driving test cycle, the number of second drunk-driving tests, the sensitivity level of the drinking sensor 120, the size of a critical value, etc.

That is, the first drunk-driving test may be performed by the comparing of an alcohol concentration acquired based on the information sensed through the drinking sensor 120 with a preset, critical value. For example, when the acquired alcohol concentration exceeds the critical value, the processor 170 may determine that a driver has drunk, and when the acquired alcohol concentration is lower than or equal to the critical value, it is possible to determine that the driver has not drunk.

In addition, the processor 170 may set the test condition based on the acquired alcohol concentration when the result of the first drunk-driving test satisfies normal criteria.

For example, when the alcohol concentration is low (when a difference to the critical value is large), the processor 170 may increase the second drunk-driving test cycle, decrease the number of second drunk-driving tests, decrease the sensitivity level or increase the size of the critical value.

Also, when the alcohol concentration is high (when a difference to the critical value is small), the processor 170 may decrease the second drunk-driving test cycle, increase the number of second drunk-driving tests, increase the sensitivity level or decrease the size of the critical value.

Also, when the test condition is set, the processor 170 performs the second drunk-driving test based on the set test condition, in step S150.

The second drunk-driving test may be performed by the drinking sensor 120 in the vehicle 700.

In some implementations, the second drunk-driving test may be performed through the analysis of an alcohol concentration in the air inside the vehicle, an alcohol concentration acquired through the biometric signal of a driver, the driving pattern of the vehicle 700, the voice of a passenger in the vehicle, etc.

That is, the processor 170 may actuate a sensor that senses an alcohol concentration in the air in the vehicle among drinking sensors 120 in the vehicle, in order to perform the second drunk-driving test.

In some implementations, the alcohol concentration in the air in the vehicle includes both the alcohol concentration of the driver in the vehicle and the alcohol concentration of a passenger.

Thus, when the passenger has drunk and the driver has not drunk, the sensed alcohol concentration may not become accurate information for performing the first drunk-driving test or second drunk-driving test of the driver.

Thus, when the acquired alcohol concentration is higher than the critical value, the first drunk-driving test and the second drunk-driving test have no trouble, but when the acquired alcohol concentration is higher than the critical value, the first drunk-driving test and the second drunk-driving test have trouble.

Thus, when the alcohol concentration in the air in the vehicle is acquired, the processor 170 further determines whether the acquired alcohol concentration is caused by the driver of the vehicle or by the passenger. This may be performed by a separate drinking sensor 120 in the vehicle.

In addition, since the first drunk-driving test or second drunk-driving test may be performed by the passenger, the processor 170 performs user authentication together to further check whether the drunk-driving test has been performed by the driver in the driver's seat, when the first drunk-driving test or second drunk-driving test are performed.

Also, when the first or second drunk-driving test is performed by the alcohol concentration in the air in the vehicle, the processor 170 checks the window state of the vehicle at the time when the first or second drunk-driving test is performed.

In addition, when the window state of the vehicle is a closed state, the processor 170 performs the first or second drunk-driving test based on the alcohol concentration in the air in the vehicle.

In some implementations, when the window state of the vehicle is an open state, the processor 170 does not use the alcohol concentration in the air in the vehicle as information for performing the first or second drunk-driving test.

In some implementations, when the window state of the window is an open state, the processor 170 changes the window state of the vehicle to a closed state, and after the window state of the vehicle is changed to the closed state, the alcohol concentration in the air in the vehicle is acquired.

Also, the processor 170 may actuate a sensor that senses an alcohol concentration based on a touch signal among drinking sensors 120 in the vehicle, in order to perform the second drunk-driving test.

The alcohol concentration sensed based on the touch signal may be acquired based on the biometric signal of the driver that is acquired by a touch of the driver.

In some implementations, in order to acquire the alcohol concentration based on the touch signal as described above, a touch signal input from the driver is required. Thus, the processor 170 output guide information so that the touch signal may be input.

Also, the processor 170 may acquire driving information through a sensor analyzing the driving pattern of the vehicle 700 in order to perform the second drunk-driving test.

In order to analyze the driving pattern, the processor 170 acquires at least one of vehicle 700 direction information, position information, speed information, acceleration information, tilt information, forward/backward movement information, fuel information, information on the distance to front and rear vehicles 700, information on the distance between a vehicle 700 and a lane, and turn signal information.

Also, the processor 170 acquires voice generated in the vehicle in order to perform the second drunk-driving test and analyzes the acquired voice. In addition, the processor 170 performs the second drunk-driving test based on a result of the voice analysis.

For example, when the words in the voice include a drinking related word, such as "alcohol" or "chauffeur service", the processor 170 may determine that the driver has drunk.

Subsequently, the processor 170 determines whether the result of the second drunk-driving test satisfies the normal criteria, in step S160.

In addition, when as a result of the determination in step S160, the result of the second drunk-driving test satisfies the normal criteria, the processor 170 maintains the current driving state of the vehicle 700, in step S170.

Figure 7:
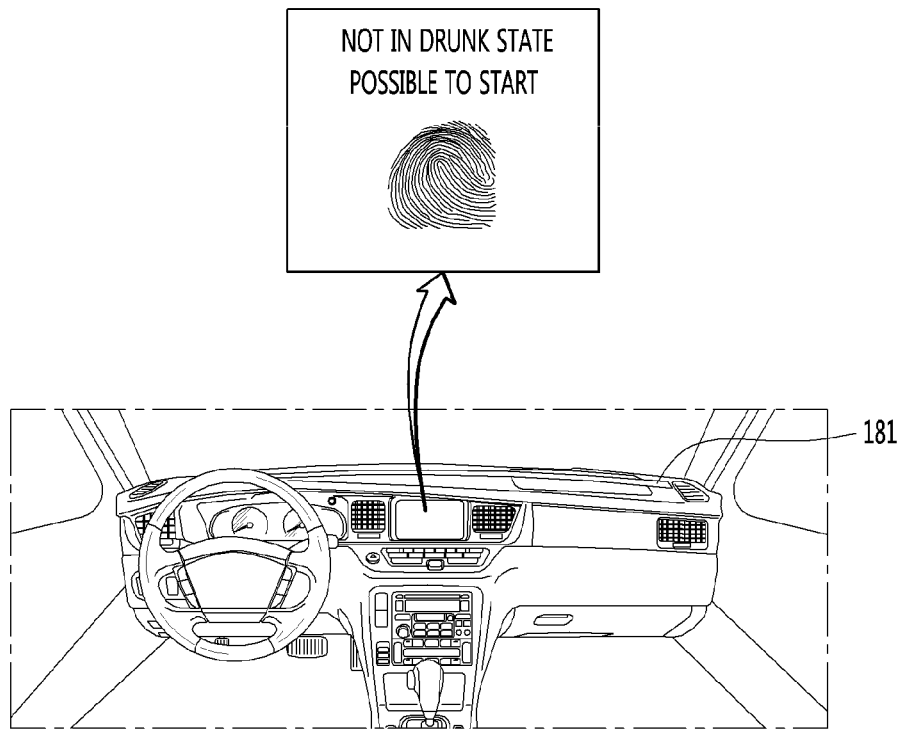

In some implementations, information notifying that the result of the drunk-driving test (including the first drunk-driving test and the second drunk-driving test) satisfies the normal criteria may be displayed on the display unit 180 as shown in FIG. 7.

Also, when as a result of the determination in step S160, the result of the second drunk-driving test does not satisfy the normal criteria, the processor 170 changes the driving state of the vehicle 700, in step S180.

That is, when the result of the second drunk-driving test does not satisfy the normal criteria, the processor 170 automatically controls the vehicle so that the vehicle stops in a nearby, safe region.

Figure 8:
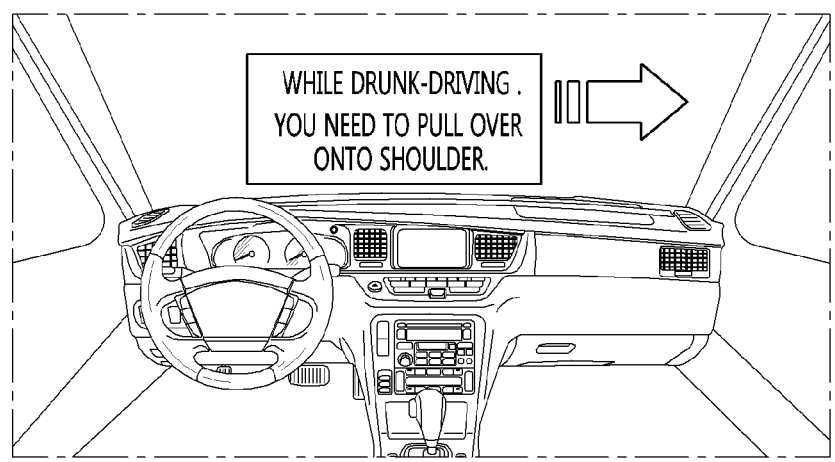

In some implementations, information notifying that the vehicle has pulled over onto the nearby shoulder because the result of the second drunk-driving test does not satisfy the normal criteria may be output to the display unit 180, as shown in FIG. 8.

Also, when the result of the second drunk-driving test satisfies the normal criteria, the processor 170 switches the driving mode of the vehicle to a self-driving mode.

Figure 9:
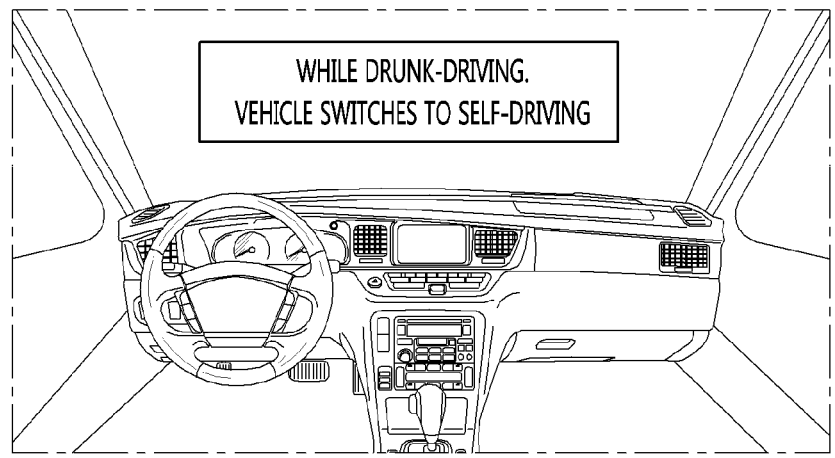

In some implementations, information notifying that the driving mode is switched to the self-driving mode may be output to the display unit 180, as shown in FIG. 9.

Figure 10:

Also, the processor 170 notifies an adjacent vehicle whether the vehicle 700 has drunk-driven. To this end, the processor 170 performs communication with a nearby vehicle through the communication unit 120 to transmit information for notifying whether drunk-driving has been performed. Also, the processor 170 may output, through a separate display unit, information notifying that the vehicle 700 is a drunk-driving vehicle, as shown in FIG. 10.

Figure 11:
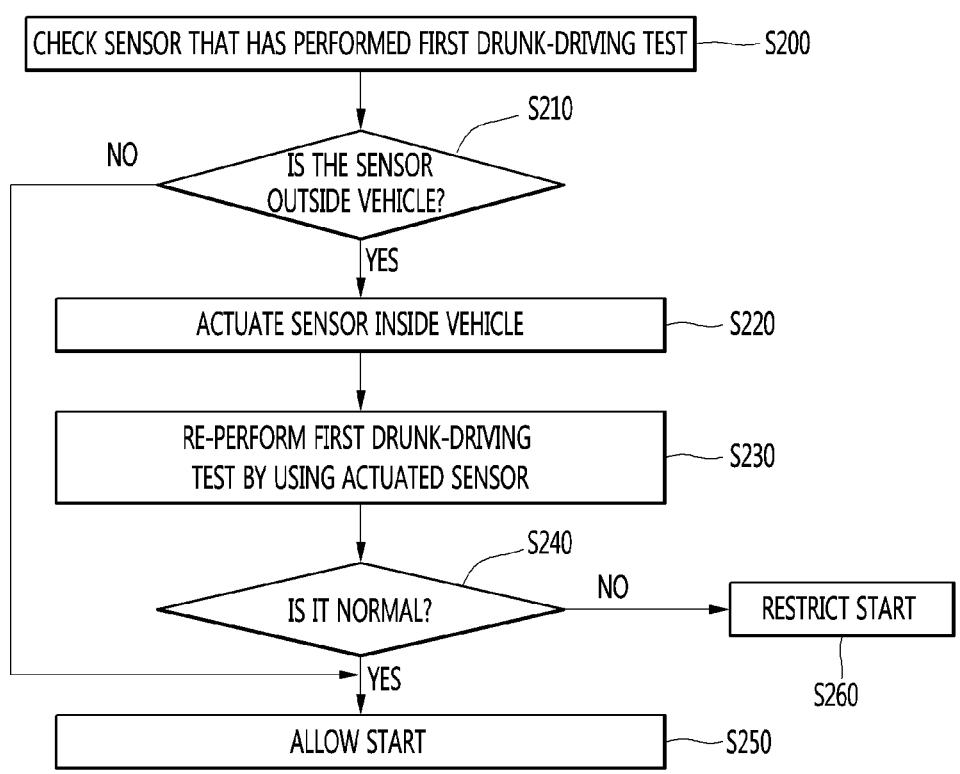

Next, referring to FIG. 11, the processor 170 checks the type of a sensor performing the first drunk-driving test when the first drunk-driving test is performed, in step S200.

That is, the processor 170 determines whether the sensor that has performed the first drunk-driving test is a sensor inside or outside the vehicle.

In addition, the processor 170 determines based on a result of the check whether the sensor that has performed the first drunk-driving test is a sensor outside the vehicle, in step S210.

Subsequently, when as a result of the determination in step S210, the sensor is a sensor outside the vehicle, the processor 170 actuates sensors inside the vehicle excluding sensors outside the vehicle, in step S220.

In addition, the processor 170 re-performs the first drunk-driving test by using the actuated sensors in step S230.

That is, when the first drunk-driving test is performed outside the vehicle, a driver in the driver's seat of the vehicle may be different from a person on which the first drunk-driving test has been performed outside the vehicle and thus the processor 170 performs the first drunk-driving test after the driver gets in the vehicle.

In addition, the processor 170 determines whether the result of the first drunk-driving test re-performed satisfies the normal criteria, in step S230.

In addition, when the first drunk-driving test is normally re-performed, the processor 170 allows the start of the vehicle 700 in step S250, and if negative, the processor restricts the start of the vehicle 700 in step S260.

Figure 12:
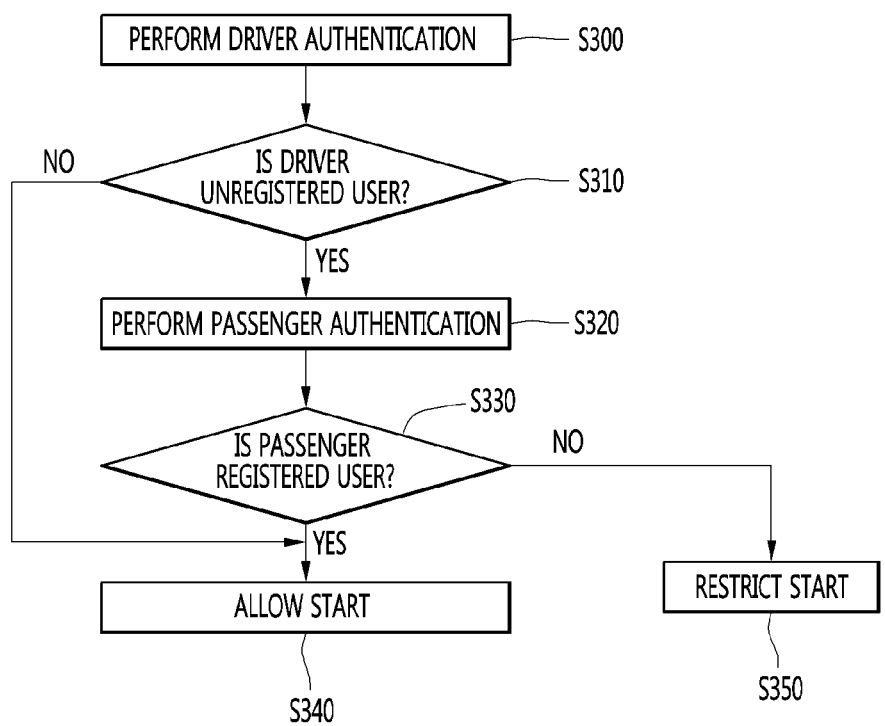

Also, referring to FIG. 12, the processor 170 performs user authentication on the driver in the driver sear of the vehicle 700 when the first drunk-driving test and the second drunk-driving test are performed, in step S300.

In addition, as a result of the user authentication, the processor 170 determines whether the driver is a registered user, in step S310.

Subsequently, the processor 170 may restrict the start or driving of the vehicle 700 when the driver is an unregistered user.

In some implementations, when the driver is an unregistered user, the processor 170 performs user authentication on a passenger in the vehicle, in step S320.

In addition, when the passenger is a registered user, the processor 170 allows the start of the vehicle 700 in step S340.

Also, when both the driver and the passenger are unregistered users, the processor 170 restricts the start and driving of the driving 700 in step S350.

Also, when the driver is a registered user, the processor 170 allows the start of the vehicle 700.

Figure 13:
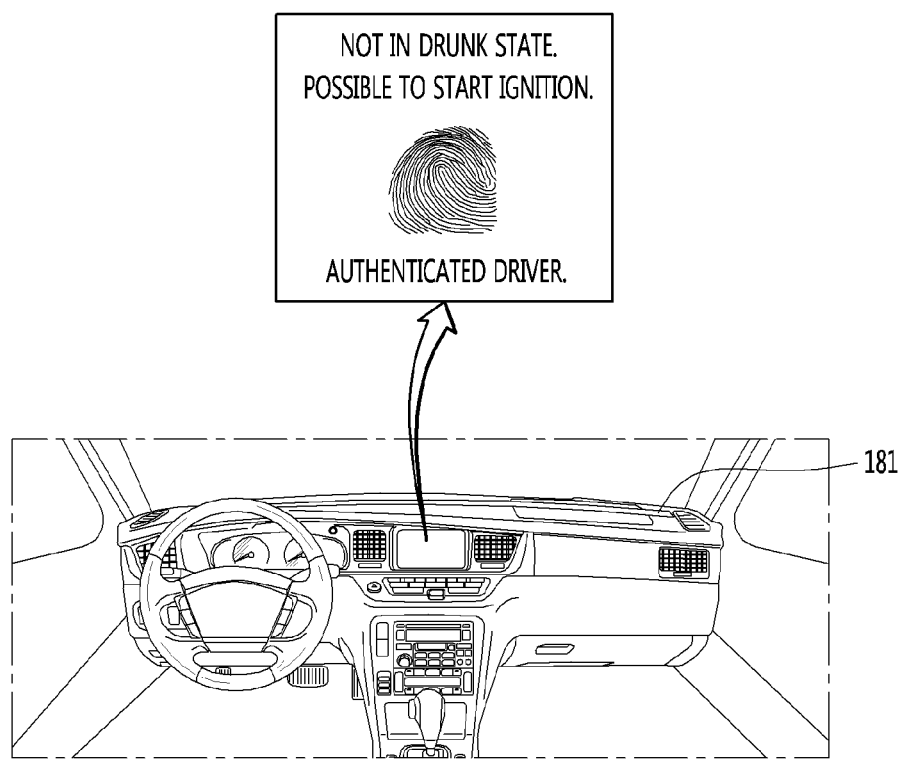

That is, when the driver is a registered driver and the result of the drunk-driving test satisfies the normal criteria, information notifying them may be output through the display unit 180, as shown in FIG. 13.

Figure 14:
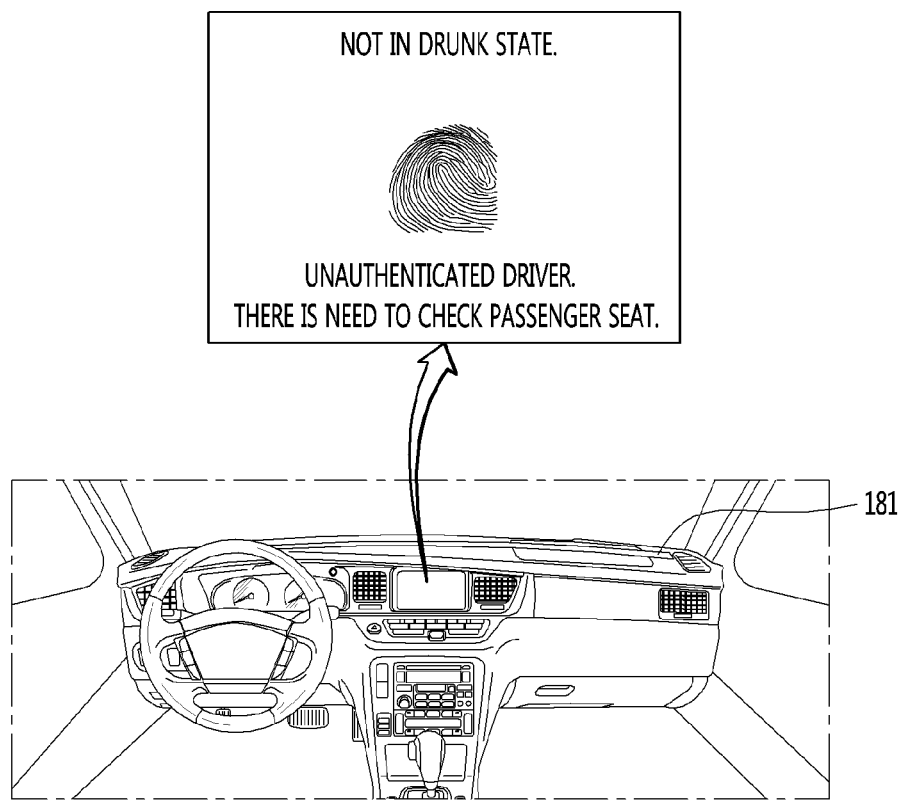

Also, when the driver is an unregistered driver, information notifying that the drunk-driving test on the driver satisfies the normal criteria but user authentication on a passenger is required may be output through the display unit 180, as shown in FIG. 14.

Figure 15:
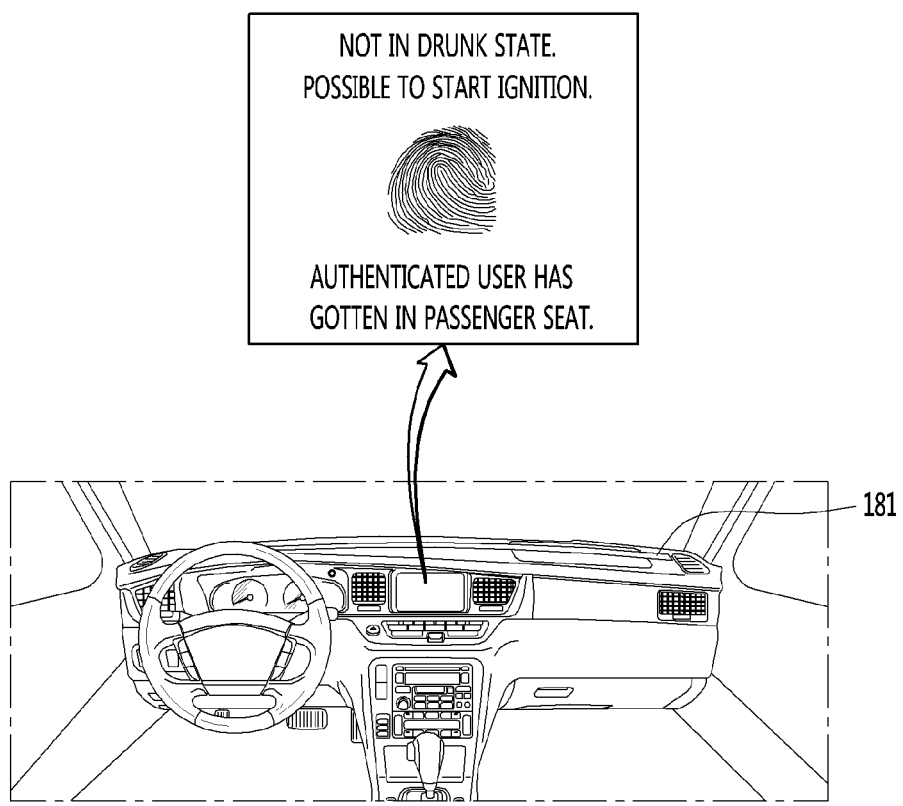

Also, when the passenger is a registered driver, information notifying that a registered user has gotten in a passenger seat, not the driver's seat may be output through the display unit 180, as shown in FIG. 15.

Figure 16:
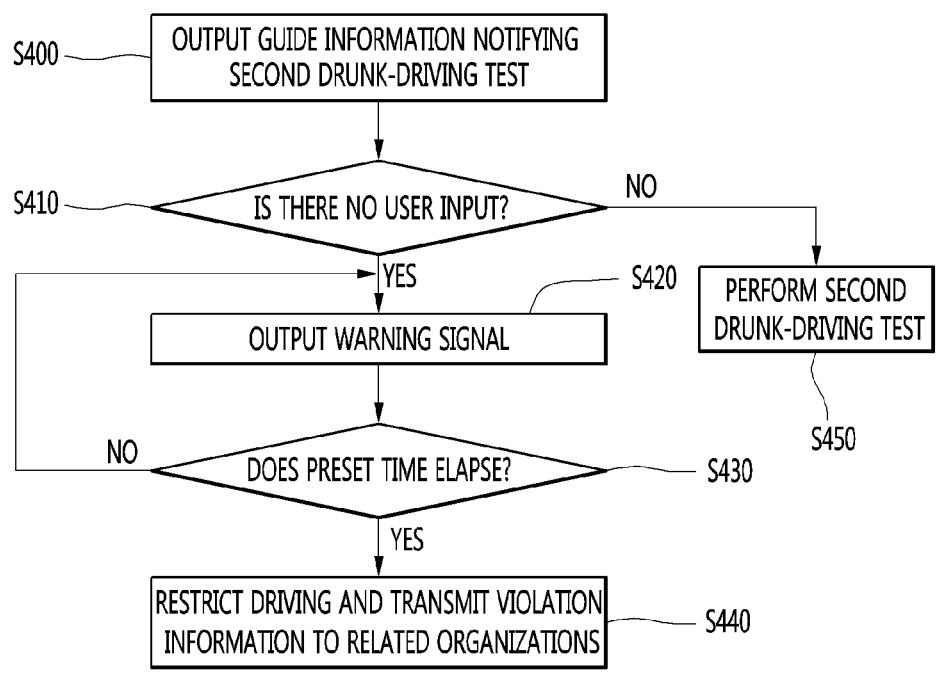

Referring to FIG. 16, when it is time to perform the second drunk-driving test and a user input for the second drunk-driving test is required, the processor 170 outputs, through the display unit 180, information notifying that the user input is required and information notifying that the second drunk-driving test is performed, in step S400.

Figure 17:
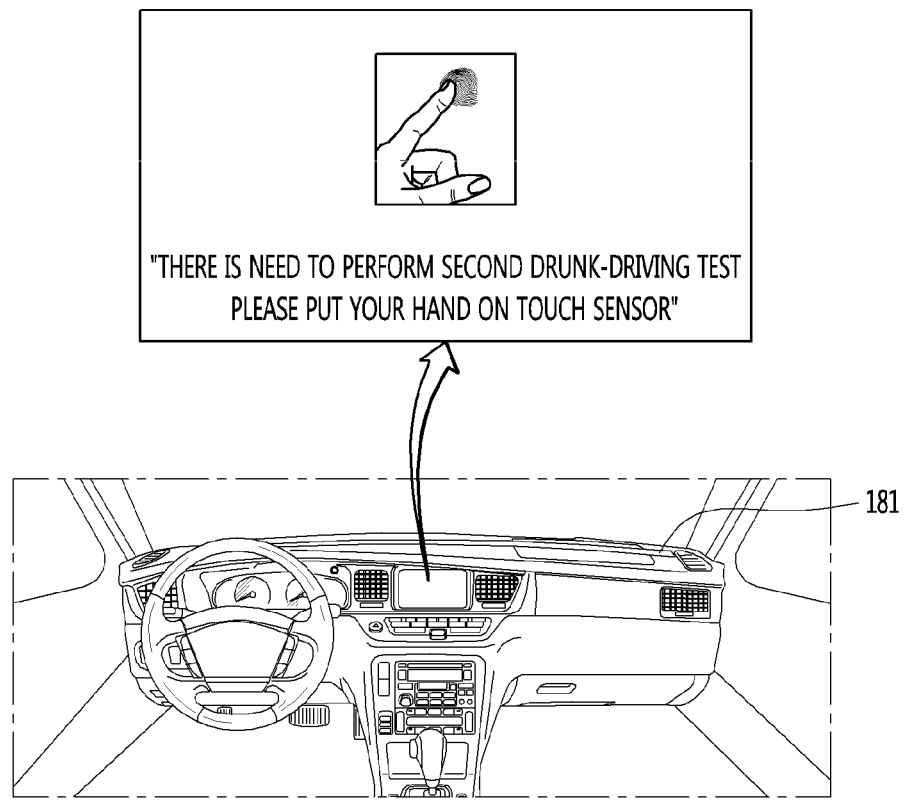

That is, information enabling the second drunk-driving test to be normally performed, such as a message "The second drunk-driving test is performed. Please put your hand on the touch sensor." may be output on the display unit 180, as shown in FIG. 17.

Subsequently, the processor 170 determines whether there is no user input for the second drunk-driving test even after the information is output, in step S410.

In addition, when there is no user input, the processor 170 outputs a warning signal causing the user input in step S420.

In addition, the processor 170 determines whether there is still no user input until a preset time elapses after the warning signal is output, in step S430.

In addition, when there is no user input, the processor 170 restricts the driving of the vehicle 700 and transmits, to a related organization, information notifying that the result of the second drunk-driving test on the vehicle does not satisfy the normal criteria, in step S440.

Also, when there is the user input, the processor 170 performs the second drunk-driving test based on the user input in step S450.

The second drunk-driving test may be suddenly performed at a specific time based on a preset cycle or irregular cycle.

In some implementations, the second drunk-driving test may be performed when a preset event occurs. For example, the second drunk-driving test may be performed when a driver in the driver's seat of the vehicle 700 is replaced.

Figure 18:
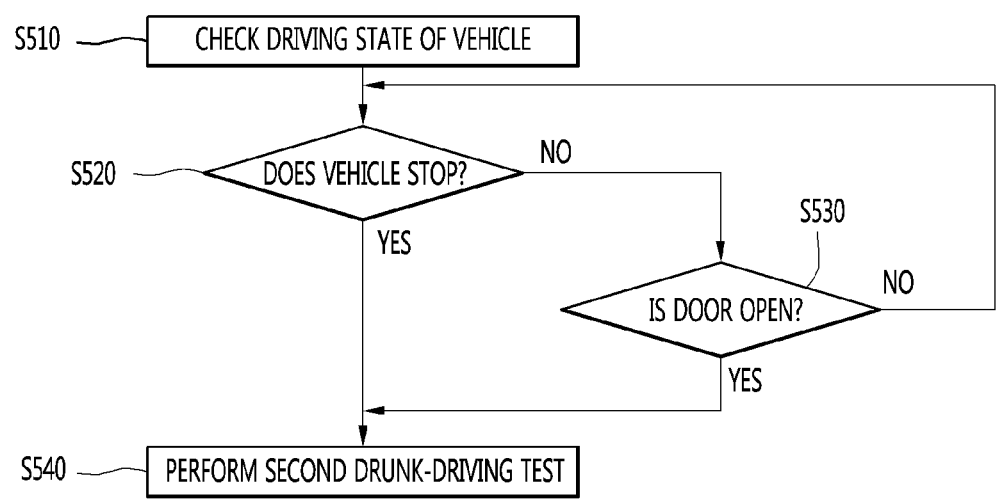

That is, referring to FIG. 18, the processor 170 regularly checks the driving state of the vehicle 700 in step S510.

In addition, the processor 170 determines based on the driving state whether the vehicle 700 has stopped, in step S520.

Also, when the vehicle has not stopped, the processor 170 determines whether the door of the vehicle has opened, in step S530.

In addition, when the vehicle 700 has stopped or the door of the vehicle has opened, the processor 170 performs the second drunk-driving test in step S540.

Also, it is possible to increase accuracy in drunk-driving test by performing the first drunk-driving test before the start of the vehicle and further performing the second drunk-driving test during the driving of the vehicle.

Also, it is possible to provide an optimal drunk-driving test environment depending on the situation, by applying a result of the first drunk-driving test to change the condition for the second drunk-driving test.

Also, it is possible to prevent counterfeit actions, such as a test by another person by further performing the first drunk-driving test after the driver gets in the vehicle, when the first drunk-driving test is performed before the driver gets in the vehicle.

Also, it is possible to prevent vehicle theft by performing user authentication on a driver and passengers to allow the start of the vehicle only when there are registered users inside the vehicle.

Also, it is possible to efficiently prepare for the replacement of a driver that may occur during the driving of the vehicle, by further performing the second drunk-driving test when the door of the vehicle opens or the vehicle stops.

Also, it is possible to prevent an accident that may occur by the drunk-driving of the driver, by restricting the driving of the vehicle, transmitting information on the vehicle to a related organization or changing the driving mode of the vehicle to a self-driving mode, when the result of the second drunk-driving test on the driver does not satisfy normal criteria.

Figure 19:
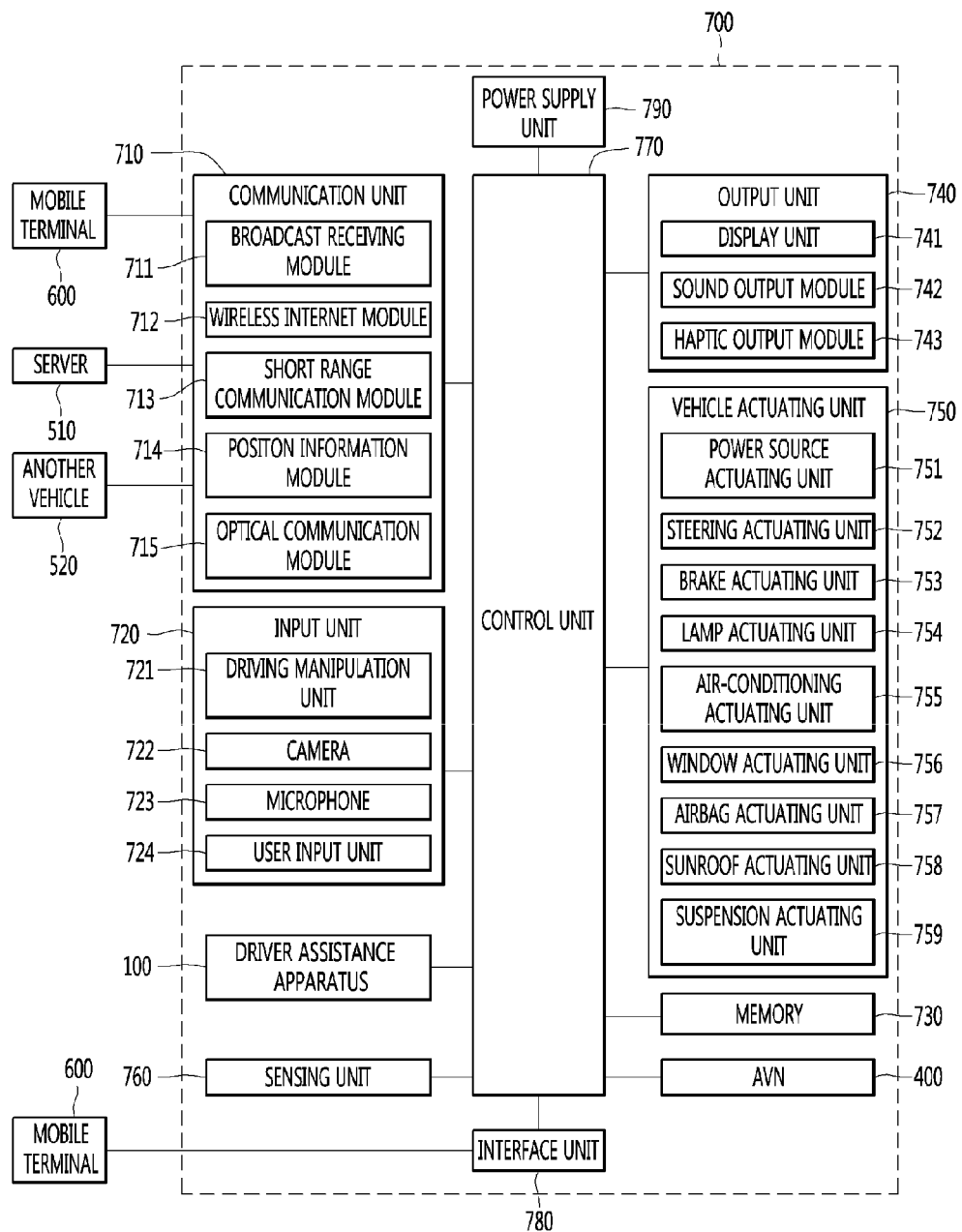
FIG. 19 is a diagram illustrating example elements of a vehicle.

FIG. 19 is an example of an internal block diagram of the vehicle of FIG. 1.

Such a driver assistance apparatus 100 may be included in the vehicle.

The vehicle may include a communication unit 710, an input unit 720, a sensing unit 760, an output unit 740, a vehicle actuating unit 750, a memory 730, an interface unit 780, a control unit 770, a power supply unit 790, a driver assistance apparatus 100, and an AVN apparatus 400.

The communication unit 710 may include one or more modules that enable wireless communication between the vehicle 700 and the mobile terminal 600, between the vehicle 700 and an external sever 510, or between the vehicle 700 and another vehicle 510. Also, the communication unit 710 may include one or more modules that connect the vehicle to one or more networks.

The communication unit 710 may include a broadcast receiving module 711, a wireless internet module 712, a short-range communication module 713, a position information module 714, and an optical communication module 715.

The broadcast receiving module 711 receives a broadcast signal or broadcast related information from an external broadcast management server through a broadcast channel. In this example, a broadcast includes a radio or TV broadcast.

The wireless internet module 712 indicates a module for wireless internet access and may be built into or external to the vehicle. The wireless internet module 712 is configured to transmit/receive a wireless signal in a communication network based on wireless internet technologies.

The wireless internet technology may include Wireless LAN (WLAN), Wireless-Fidelity (Wi-Fi), Wi-Fi Direct, Digital Living Network Alliance (DLNA), Wireless Broadband (WiBro), World Interoperability for Microwave Access (WiMAX), High Speed Downlink Packet Access (HSDPA), High Speed Uplink Packet Access (HSUPA), Long Term Evolution (LTE), and Long Term Evolution-Advanced (LTE-A) and the wireless internet module 712 transmits/receives data based on at least one wireless internet technology including internet technologies not listed above. For example, the wireless internet module 712 may exchange data with the external server 510 wirelessly. The wireless internet module 712 may receive weather information or road traffic information (e.g., TPEG) from the external server 510.

The short-range communication module 713 may support short-range communication by using at least one of Bluetooth™, Radio Frequency Identification (RFID), Infrared Data Association (IrDA), Ultra Wideband (UWB), ZigBee, Near Field Communication (NFC), Wireless-Fidelity (Wi-Fi), Wi-Fi Direct, and Wireless Universal Serial Bus (Wireless USB) technologies.

Such a short-range communication module 713 may form a Wireless Area Network (WAN) to perform short-range communication between the vehicle and at least one external device. For example, the short-range communication module 713 may exchange data with the mobile terminal 600. The short-range module 713 may receive weather information or road traffic information (e.g., TPEG) from the mobile terminal 600. If a user gets in the vehicle, the mobile terminal 600 of the user and the vehicle is configured to perform pairing on each other automatically or by the execution of an application by the user.

The position information module 714 is a module for acquiring the position of the vehicle and includes a GPS module as a typical example. For example, the vehicle may use a signal transmitted by a GPS satellite to acquire the position of the vehicle, when the GPS module is used.

The optical communication module 715 may include a light transmission unit and a light reception unit.

The light reception unit may convert a light signal into an electrical signal to receive information. The light reception unit may include a photo diode (PD) for receiving light. The PD may convert light into an electrical signal. For example, the light reception unit may receive information on the front vehicle through light emitted from a light source that is included in the front vehicle.

The light transmission unit may include at least one light-emitting element for converting an electrical signal into a light signal. In this example, the light-emitting element may be a light-emitting diode (LED). The light transmission unit may convert an electrical signal into a light signal to transmit the light signal to the outside. For example, the light transmission unit may transmit the light signal to the outside through the on/off of the light-emitting element corresponding to a predetermined frequency. Also, the light transmission unit may include a plurality of light-emitting element arrays. Also, the light transmission unit may be integrated into a lamp that is installed at the vehicle. For example, the light transmission unit may be at least one of a headlight, a taillight, a stop lamp, a turn signal, and a sidelight. For example, the optical communication module 715 may exchange data with the other vehicle 520 through optical communication.

The input unit 720 may include the driving manipulation units 721, a camera 195, a microphone 723, and a user input unit 724.

The driving manipulation units 721 receives a user input for driving the vehicle. (See FIG. 2 for the following description.) The driving manipulation units 721 may include the steering input units 721A, a shift input units 721D, an acceleration input units 721C, and a brake input units 721B.

The steering input units 721A receives an input for the driving direction of the vehicle from a user. The steering input units 721A may be formed in the form of a wheel so that a steering input may be performed by rotation. Also, the steering input units 721A may also be formed as a touch screen, touch pad or button.

The shift input units 721D receives an input for the parking P, driving, neutrality N, and rear movement R of the vehicle from the user. The shift input units 721D may be formed in the form of a lever. Also, the shift input units 721D may also be formed as a touch screen, touch pad or button.

The acceleration input units 721D receives an n input for the acceleration of the vehicle from the user. The brake input units 721B receives an input for the speed decrease of the vehicle from the user. The acceleration input units 721C and the brake input units 721B may be formed in the form of a pedal. Also, the acceleration input units 721C or the brake input units 721B may also be formed as a touch screen, touch pad or button.

The camera 722 may include an image sensor and an image processing module. The camera 722 may process a still image or video that is obtained by an image sensor (e.g., CMOS or CCD). The image processing module may process the still image or video acquired by the image sensor to extract necessary information and transmit the extracted information to the processor 770. The vehicle may include the camera 722 that captures images in front of the vehicle or images around the vehicle, and the monitoring unit that captures an image of the interior of the vehicle.

The monitoring unit may acquire an image of a passenger. The monitoring unit may acquire the image of the passenger for biometrics.

Although FIG. 19 shows that the monitoring unit and the camera 722 are included in the input unit, the camera 722 may also be included in the driver assistance apparatus as described above.

The microphone 723 may process an external sound signal into electrical data. The processed data may be used in various methods based on a function that is executed at the vehicle. The microphone 723 may convert a user's voice command into electrical data. The electrical data obtained through conversion may be transmitted to the control unit 770.

In some implementations, the camera 722 or the microphone 723 may also be a component that is included in the sensing unit 760, and not in the input 720.

The user input unit 724 receives information from the user. When information is input through the user input unit 724, the control unit 770 is configured to control the operation of the vehicle corresponding to the input information. The user input unit 724 may include a touch-type input units or mechanical input units. The user input unit 724 may be disposed at a region of a steering wheel. In some implementations, a driver may manipulate the user input unit 724 with his or her finger, holding the steering wheel.

The sensing unit 760 senses a signal relating to the driving of the vehicle. To this end, the sensing unit 760 may include a wheel sensor, a speed sensor, a tilt sensor, a weight sensor, a heading sensor, a yaw sensor, a gyro sensor, a position module, a vehicle forward/backward movement sensor, a battery sensor, a fuel sensor, a tire sensor, a steering sensor by steering wheel rotation, a vehicle temperature sensor, a vehicle humidity sensor, an ultrasonic sensor, a radar, a Lidar, and so on.

Thus, the sensing unit 760 may acquire sensing signals for vehicle collision information, vehicle direction information, vehicle position information (GPS information), vehicle angle information, vehicle speed information, vehicle acceleration information, vehicle tilt information, vehicle forward/backward movement information, battery information, fuel information, tire information, vehicle lamp information, vehicle temperature information, vehicle humidity information, steering wheel rotation angle, and so on.

The sensing unit 760 may further include an acceleration pedal sensor, a barometric pressure sensor, an engine speed sensor, an Air Flow Sensor (AFS), an Air Temperature Sensor (ATS), a Water Temperature Sensor (WTS), a Throttle Position Sensor (TPS), a TDC sensor, a Crank Angle Sensor (CAS), and so on.

The sensing unit 760 may include a biometric recognition information sensing unit. The biometric recognition information sensing unit senses and acquires biometric recognition information on a passenger. The biometric recognition information may include fingerprint information, iris-scan information, retina-scan information, hand geometry information, facial recognition information, and voice recognition information. The biometric recognition information sensing unit may include a sensor that senses biometric recognition information of the passenger. In some implementations, the monitoring unit and the microphone 723 may operate as sensors. The biometric recognition information sensing unit may acquire hand geometry information and facial recognition information through the monitoring unit.

The output unit 740 is used for outputting information processed by the control unit 770 and may include the display unit 741, the sound output unit 742, and the haptic output unit 743.

The display unit 741 may display information processed by the control unit 770. For example, the display unit 741 may display vehicle related information. In this example, the vehicle related information may include vehicle control information for direct control over the vehicle or driver assistance information for a driving guide for a driver. Also, the vehicle related information may include vehicle state information that indicates the current state of the vehicle, or vehicle operation information relating to the operation of the vehicle.

The display unit 741 may include at least one of an LCD, a TFT LCD, an OLED, a flexible display, a 3D display, and an e-ink display.

The display unit 741 may form a mutual layer structure with a touch sensor or be integrally formed to implement a touch screen. The touch screen may function as the user input unit that provides an input interface between the vehicle and the user, and also provide an output interface between the vehicle and the user. In some implementations, the display unit 741 may include a touch sensor sensing a touch of the display unit 741 to be capable of receiving a control command by the touch. Accordingly, when the display unit 741 is touched, the touch sensor senses the touch, and the control unit 770 may generate, based on the touch, a control command corresponding to the touch. A thing input by the touch may be a letter, a number, or a menu item that may be instructed or designated in various modes.

The display unit 741 may include a cluster so that a driver may see vehicle state information or vehicle operation information simultaneously with driving. The cluster may be located on the dashboard. In some implementations, the driver may see information displayed on the cluster, maintaining forward view.

Also, the the display unit 741 may be implemented as a HUD. When the display unit 741 is implemented as the HUD, it is possible to output information through a transparent display that is installed on the windshield. In some implementations, the display unit 741 may include a projection module to output information by using image that is projected onto the windshield.

The sound output unit 742 converts an electrical signal from the control unit 770 into an audio signal and outputs the audio signal. To this end, the sound output unit 742 may include a speaker and so on. The sound output unit 742 may also output sound corresponding to the operation of the user input unit 724.

The haptic output unit 743 generates a haptic output. For example, the haptic output unit 743 may enable a steering wheel, a safety belt and a seat to vibrate so that a user may recognize an output.

The vehicle actuating unit 750 is configured to control the operations of various apparatuses of the vehicle. The vehicle actuating unit 750 may include a power source actuating unit 751, a steering actuating unit 752, a brake actuating unit 753, a lamp actuating unit 754, an air-conditioning actuating unit 755, a window actuating unit 756, an airbag actuating unit 757, a sunroof actuating unit 758, and a suspension actuating unit 759.

The power source actuating unit 751 is configured to perform electronic control over the power source in the vehicle.

For example, when the power source is a fossil fuel based engine (not shown), the power source actuating unit 751 is configured to perform electronic control over the engine. Thus, it is possible to control the output torque of the engine. When the power source actuating unit 751 is the engine, it is possible to restrict the output torque of the engine to restrict the speed of the vehicle.

As another example, when the power source is an electricity based motor (not shown), the power source actuating unit 751 is configured to control the motor. Thus, it is possible to control the speed, torque and so on of the motor.

The steering actuating unit 752 is configured to perform electronic control over a steering apparatus in the vehicle. Thus, it is possible to change the driving direction of the vehicle.

The brake actuating unit 753 is configured to perform electronic control over a brake apparatus in the vehicle. For example, it is possible to control the operation of a brake installed at a wheel to decrease the speed of the vehicle. As another example, by enabling brakes disposed at the left wheel and the right wheel respectively to perform different operations, it is possible to adjust the driving direction of the vehicle to the left or to the right.

The lamp actuating unit 754 is configured to control the turn on/off of lamps that are disposed inside and outside the vehicle. Also, it is possible to control the intensity, direction and so on of light emitted from the lamp. For example, it is possible to control a turn signal lamp, a brake lamp, and so on.

The air-conditioning actuating unit 755 is configured to perform electronic control over an air conditioner in the vehicle. For example, when the temperature inside the vehicle is high, it is possible to operate the air conditioner so that cold air is supplied into the vehicle.

The window actuating unit 756 is configured to perform electronic control over a window apparatus in the vehicle. For example, it is possible to open or close left and right windows of the vehicle.

The airbag actuating unit 757 is configured to perform electronic control over an airbag apparatus in the vehicle. For example, it is possible to operate an airbag in a risky situation.

The sunroof actuating unit 758 is configured to perform electronic control over a sunroof apparatus in the vehicle. For example, it is possible to open or close the sunroof.

The suspension actuating unit 759 is configured to perform electronic control over a suspension apparatus in the vehicle. For example, when the road surface is uneven, it is possible to control a suspension apparatus to reduce the vibration of the vehicle.

The memory 730 is coupled to the control unit 770. The memory 770 may store fundamental data on units, control data for operation control over the units, and input and output data. The memory 790 may be various storage devices, such as a ROM, RAM, EPROM, flash drive, and hard drive that are hardware. The memory 730 may store various pieces of data for the overall operations of the vehicle, such as programs for processing or controlling by the control unit 770.

The interface 730 may function as a path to various kinds of external devices that are connected to the vehicle. For example, the interface unit 780 may include a port connectable to the mobile terminal 600 and be connected to the mobile terminal 600 through the port. In some implementations, the interface unit 780 may exchange data with the mobile terminal 600.

The interface unit 780 may function as a path through which electrical energy is supplied to the mobile terminal 600. When the mobile terminal 600 is coupled to the interface unit 780, the interface unit 780 supplies electrical energy supplied from the power supply unit 790 to the mobile terminal 600 based on the control of the control unit 770.

The control unit 770 is configured to control the overall operation of each unit in the vehicle. The control unit 770 may be named an electronic control unit (ECU).

Such a control unit 770 may execute a function corresponding to a transmitted signal, based on the execution signal transmission of the driver assistance apparatus.

The control unit 770 may be implemented by using at least one of an ASIC, a DSP, a DSPD, a PLD, an FPGA, a processor, a controller, a micro-controller, a microprocessor, and other electrical units for executing functions.

The control unit 770 is configured to perform the role of the above-described processor 170. That is, the processor 170 of the driver assistance apparatus may be set directly to the control unit 770 of the vehicle.

In some implementations, the control unit 770 may also control components to transmit information requested by the processor 170.

The power supply unit 790 may supply power required for the operation of each component based on the control of the control unit 770. In particular, the power supply unit 770 may receive power from a battery in the vehicle. The AVN apparatus 400 may exchange data with the control unit 770. The control unit 770 may receive navigation information from the AVN apparatus 400 or a separate navigation apparatus (not shown). In this example, the navigation information may include set destination information, route information based on the destination, vehicle driving related map information, or vehicle position information.

What is claimed is:

1. A driver assistance apparatus comprising:
a sensor unit configured to measure an alcohol concentration from a driver, and output the measured alcohol concentration, wherein the sensor unit comprises at least one of a first sensor disposed at an external door handle of a vehicle or a second sensor disposed at a vehicle remote key; and
a processor configured to:
perform a first drunk-driving test based on a first alcohol concentration received from the at least one of the first sensor or the second sensor before the driver gets in the vehicle, and
perform a second drunk-driving test based on a second alcohol concentration received from the sensor unit while the vehicle is operating,
wherein the sensor unit is configured to:
sense at least one of information on the driver touching a touch sensor, information on a driving pattern based on a usage of a steering wheel, information on an alcohol level in air inside the vehicle, or information on a conversation pattern of a passenger in the vehicle, and
output, to the processor, the information for the second drunk-driving test, and wherein the processor is configured to:
monitor whether one or more windows of the vehicle are opened or closed during performance of the second drunk-driving test, and
control, in response to monitoring whether the one or more windows of the vehicle are opened or closed during performance of the second drunk-driving test, the one or more windows.

2. The driver assistance apparatus of claim 1, wherein the processor is configured to:
prevent, based on a determination that the first alcohol concentration does not satisfy a critical value, starting of the vehicle, and
enable, based on a determination that the first alcohol concentration satisfies the critical value, starting of the vehicle.

3. The driver assistance apparatus of claim 1, wherein the sensor unit further comprises at least one of:
a third sensor disposed at a steering wheel of the vehicle,
a fourth sensor disposed inside the vehicle to receive a touch signal, or
a fifth sensor disposed inside the vehicle to measure an alcohol level in air inside the vehicle, and
wherein the processor is configured to perform the second drunk-driving test based on the second alcohol concentration being received from one of the second sensor, the third sensor, the fourth sensor, or the fifth sensor.

4. The driver assistance apparatus of claim 3, wherein the processor is further configured to perform, based on a determination that the first alcohol concentration is measured before the driver gets in the vehicle, a third drunk-driving test after the driver gets into the vehicle.

5. The driver assistance apparatus of claim 3, wherein the processor is further configured to verify, based on a determination that the first alcohol concentration satisfies a critical value, that the first alcohol concentration is an alcohol concentration of the driver in a driver's seat.

6. The driver assistance apparatus of claim 4, further comprising a user authentication unit that is configured to identify the driver in a driver's seat of the vehicle.

7. The driver assistance apparatus of claim 6, wherein the user authentication unit comprises at least one of:
a first user authentication unit configured to capture an image of the driver in the driver's seat and identify the driver based on the captured image, or
a second user authentication unit configured to recognize a fingerprint of the driver in the driver's seat.

8. The driver assistance apparatus of claim 6, wherein the processor is configured to restrict, based on a determination that the driver in the driver's seat of the vehicle is an unregistered driver, starting of the vehicle.

9. The driver assistance apparatus of claim 7,
wherein the user authentication unit is further configured to identify, based on a determination that the driver in the driver's seat is a registered user, a passenger in a passenger seat of the vehicle, and
wherein the processor is configured to enable, based on a determination that the passenger in the passenger seat is the registered user, starting of the vehicle.

10. The driver assistance apparatus of claim 1, wherein the processor is configured to perform the second drunk-driving test at a preset test time, wherein the preset test time is at least one of:
a first time corresponding to an irregular time,
a second time corresponding to a preset cycle,
a third time corresponding to a time that the vehicle stops, and
a fourth time corresponding to a time that a door of the vehicle opens.

11. The driver assistance apparatus of claim 1, wherein the processor is configured to:
exclude, in response to monitoring whether the one or more windows of the vehicle are opened or closed during performance of the second drunk-driving test, the information on the alcohol level in air in the vehicle for the second drunk-driving test.

12. The driver assistance apparatus of claim 1, further comprising a guide information output unit configured to provide the driver with guide information, the guide information providing instruction on how the driver provides a user input to the sensor unit.

13. The driver assistance apparatus of claim 1, further comprising a warning signal output unit that is configured to output, based on a determination that a user input for the second drunk-driving test is received or a determination that the second alcohol concentration satisfies a critical value, a warning signal.

14. The driver assistance apparatus of claim 13, wherein the warning signal output unit comprises a communication unit transmitting a result of the second drunk-driving test to a designated organization, a related organization, or a stored contact.

15. The driver assistance apparatus of claim 1, wherein the processor is configured to switch, based on a determination of a failure of the second drunk-driving test, a driving mode of the vehicle to a self-driving mode.

16. The driver assistance apparatus of claim 1, wherein the processor is configured to stop, based on a determination of a failure of the second drunk-driving test, the vehicle in a safe region.

* * * * *